United States Patent
Nakayama

(10) Patent No.: US 10,267,773 B2
(45) Date of Patent: Apr. 23, 2019

(54) PHASING ADDER, ULTRASOUND PROBE, ACOUSTIC SENSOR AND ULTRASOUND DIAGNOSIS APPARATUS

(71) Applicant: KONICA MINOLTA, INC., Chiyoda-ku, Tokyo (JP)

(72) Inventor: Yuta Nakayama, Ichikawa (JP)

(73) Assignee: KONICA MINOLTA, INC, Tokyo (JP)

( * ) Notice: Subject to any disclaimer, the term of this patent is extended or adjusted under 35 U.S.C. 154(b) by 818 days.

(21) Appl. No.: 14/634,505

(22) Filed: Feb. 27, 2015

(65) Prior Publication Data

US 2015/0260691 A1 Sep. 17, 2015

(30) Foreign Application Priority Data

Mar. 13, 2014 (JP) .................................. 2014-049692
Mar. 13, 2014 (JP) .................................. 2014-049731

(51) Int. Cl.
*G01N 29/36* (2006.01)
*G01N 29/44* (2006.01)
*G01N 29/34* (2006.01)
*G01N 29/24* (2006.01)
(Continued)

(52) U.S. Cl.
CPC ........... *G01N 29/34* (2013.01); *A61B 8/5207* (2013.01); *G01N 29/2437* (2013.01);
(Continued)

(58) Field of Classification Search
CPC ........ G01N 29/36; G01N 29/40; G01N 29/34; G01N 29/2437; G01N 29/2481;
(Continued)

(56) References Cited

U.S. PATENT DOCUMENTS

| 3,832,700 A | 8/1974 | Wu et al. |
| 2009/0040165 A1* | 2/2009 | Shimatani ............ G09G 3/3688 345/98 |
| 2014/0293739 A1* | 10/2014 | Ishihara ............... A61B 8/5207 367/11 |

FOREIGN PATENT DOCUMENTS

| JP | 48058795 U | 7/1973 |
| JP | 4947086 U | 4/1974 |

(Continued)

OTHER PUBLICATIONS

Extended European Search Report dated Jul. 21, 2015, issued in counterpart European Application No. 15157747.5.
(Continued)

*Primary Examiner* — Justin Seo
*Assistant Examiner* — Rose M Miller
(74) *Attorney, Agent, or Firm* — Holtz, Holtz & Volek PC

(57) ABSTRACT

Disclosed is a phasing adder including delay charge transfer units including holding and transferring units which obtain signal charge amounts that are not amplified and which send and receive the signal charge amounts across a predetermined plurality of stages while holding the signal charge amounts for a predetermined time in each stage and a delay adder which performs phasing addition of the signal charges which are held for a predetermined number of stages in the delay charge transfer unit, and electric capacity of each first holding unit, which is the first stage among the plurality of stages in the holding and transferring unit, where the signal charges are obtained and held at a time of ultrasound wave reception is greater than electric capacity of each of later holding units where the signal charges are to be held in a second stage and stages thereafter.

25 Claims, 11 Drawing Sheets

(51) Int. Cl.
  *H01L 27/20* (2006.01)
  *G01N 29/26* (2006.01)
  *A61B 8/08* (2006.01)
  *A61B 8/00* (2006.01)

(52) U.S. Cl.
  CPC ....... *G01N 29/2481* (2013.01); *G01N 29/262* (2013.01); *G01N 29/36* (2013.01); *H01L 27/20* (2013.01); *A61B 8/4405* (2013.01); *A61B 8/4444* (2013.01); *A61B 8/4494* (2013.01); *G01N 2291/106* (2013.01)

(58) Field of Classification Search
  CPC .. G01N 29/262; A61B 8/5207; A61B 8/4405; A61B 8/4444; A61B 8/4494; H01L 27/20
  USPC .................................................. 73/661, 602
  See application file for complete search history.

(56) References Cited

FOREIGN PATENT DOCUMENTS

| | | | |
|---|---|---|---|
| JP | 5522948 | U | 2/1980 |
| JP | 4557575 | B2 | 10/2010 |

OTHER PUBLICATIONS

Japanese Office Action (and English translation thereof) dated Nov. 21, 2017, issued in counterpart Japanese Application No. 2014-049731

\* cited by examiner

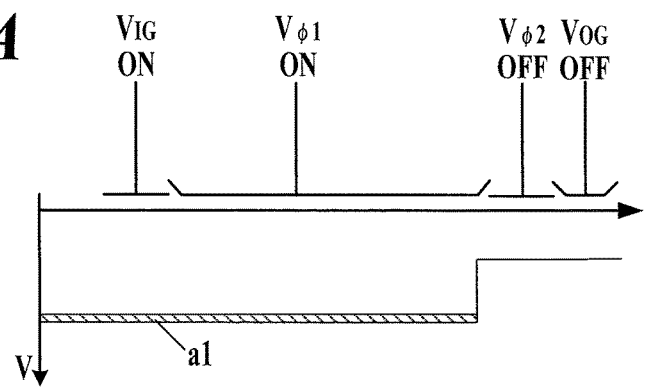
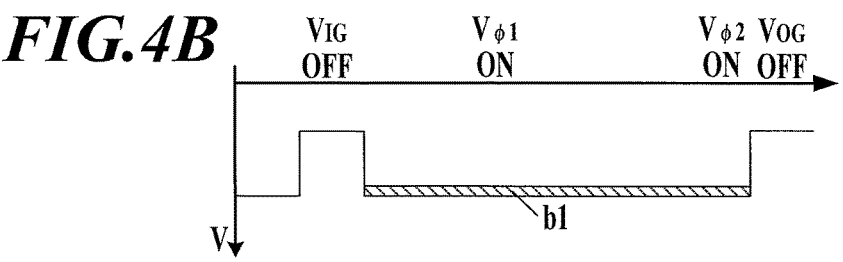
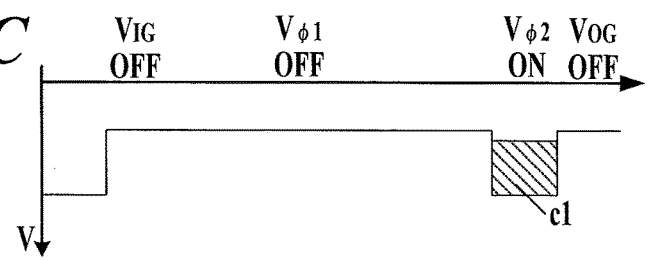
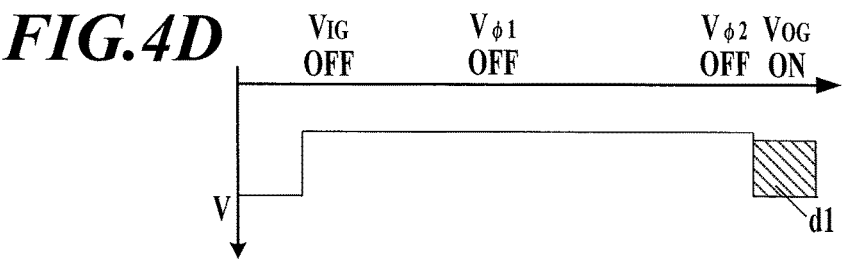

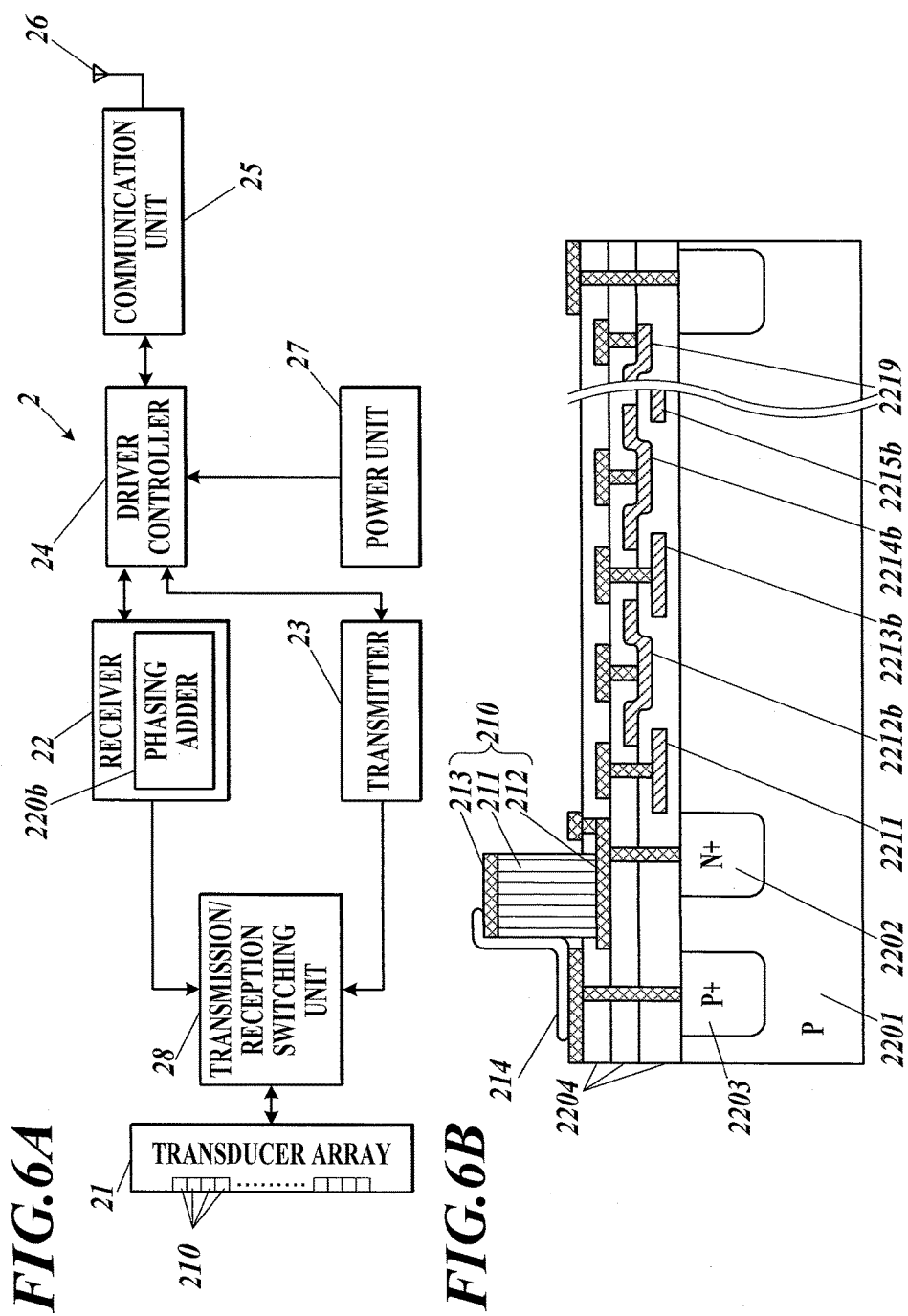

PHASING ADDER, ULTRASOUND PROBE, ACOUSTIC SENSOR AND ULTRASOUND DIAGNOSIS APPARATUS

BACKGROUND OF THE INVENTION

1. Field of the Invention

The present invention relates to a phasing adder, an ultrasound probe, an acoustic sensor and an ultrasound diagnosis apparatus.

2. Description of Related Art

A conventional ultrasound diagnosis apparatus which performs internal inspection by emitting ultrasound waves in a subject, receiving reflected waves of the ultrasound waves and analyzing the received reflected waves is known. In such ultrasound diagnosis, a subject can be examined in a non-destructive and non-invasive manner. Therefore, such ultrasound diagnosis is widely used in various purposes such as medical examinations and internal inspection of architectures.

In such ultrasound diagnosis apparatus, the received ultrasound waves are converted into electric signals according to their intensity. Converters (transducers) such as piezoelectric devices are used to receive the ultrasound waves. With respect to each ultrasound wave, the mechanical deformation (expansion and contraction) of a piezoelectric element caused by the sound pressure of the ultrasound wave is converted into an electric signal (charge amount) according to the deformation level, and this electric signal is detected.

In recent ultrasound diagnosis apparatuses, the number of piezoelectric devices for receiving ultrasound waves is increased with the demand for high accuracy in images and the sampling rate of received date has also increased. In response, power consumption has increased in the ultrasound diagnosis apparatuses. In view of the above, JP 4557575 discloses a technique to decrease power consumption by reducing the number of FGAs (Floating Gate Amplifiers) used to amplify the signals.

With respect to LNAs (Low Noise Amplifiers) which are used to convert the deformation of piezoelectric devices into electric signals, conventionally, it has been difficult to improve the signal to noise ratio (SNR) while controlling power consumption since the supply current increases according to the cutback amount of noise.

SUMMARY OF THE INVENTION

An object of the present invention is to provide a phasing adder, an ultrasound probe, an acoustic sensor and an ultrasound diagnosis apparatus which can efficiently and appropriately obtain signals from received ultrasound waves while maintaining the signal to noise ratio (SNR) and controlling power consumption.

In order to realize at least one of the above object, a phasing adder includes a delay charge transfer unit including holding and transferring units which obtain signal charge amounts that are not amplified, the signal charge amounts being obtained according to charges generated in a plurality of piezoelectric devices respectively having piezoelectric elements which generate charges in response to sound pressure of input ultrasound waves, and which send and receive the signal charge amounts across a predetermined plurality of stages while holding the signal charge amounts for a predetermined time in each stage, and a delay adder which performs phasing addition of the signal charges which are held for a predetermined number of stages in the delay charge transfer unit, wherein electric capacity (capacitance) of each first holding unit, which is the first stage among the plurality of stages in the holding and transferring unit, where the signal charges are obtained and held at a time of ultrasound wave reception is greater than electric capacity (capacitance) of each of later holding units where the signal charges are to be held in a second stage and stages thereafter.

Preferably, the electric capacities of the later holding units are equal to each other.

Preferably, the electric capacity of each first holding unit varies.

Preferably, in the phasing adder the delay charge transfer unit is formed as a semiconductor chip, and each first holding unit is connected to a corresponding piezoelectric element or is disposed near the corresponding piezoelectric element.

Preferably, an ultrasound probe includes the phasing adder, a plurality of piezoelectric devices which receive ultrasound waves and which make a plurality of first holding units respectively obtain charges, a signal amplifier which amplifies the charges which are subjected to phasing addition as a voltage signal, and a signal output unit which outputs the amplified voltage signal.

Preferably, in the ultrasound probe, electric capacities of the first holding units vary, and the first holding units include a capacity controller for setting the electric capacities of the first holding units.

Preferably, in the ultrasound probe, the signal output unit includes a wireless communication unit which outputs the signal to an external device through wireless communication.

Preferably, the ultrasound probe further comprising:
a transmission drive unit which outputs ultrasound waves of a predetermined wave length from the piezoelectric devices, and a transmission/reception switching drive unit which alternately connects the piezoelectric devices with the transmission drive unit or the delay charge transfer unit in response to a control signal.

An acoustic sensor includes the phasing adder, the plurality of piezoelectric devices which receive ultrasound waves and which make a plurality of first holding units respectively obtain charges, a signal amplifier which amplifies the charges which are subjected to phasing addition as a voltage signal, a signal output unit which outputs the amplified voltage signal, wherein in each piezoelectric device, a piezoelectric thin film is laminated directly or indirectly on a semiconductor substrate, conductivity state of a predetermined region in the semiconductor substrate changes on a basis of a charge amount induced in the piezoelectric thin film in response to sound pressure entered the piezoelectric thin film and the piezoelectric device is formed as a semiconductor chip which outputs a signal according to the conductive state to the phasing adder.

Here, the thin film is formed by various film forming methods such as spattering, CVD, sol-gel and the like.

Preferably, in the acoustic sensor, by changing conductivity level of a channel region in the semiconductor substrate due to an electric field generated by the induced charge, the conductivity state of the channel region is changed.

Preferably, in the acoustic sensor, an electrode for switching the conductivity of the channel region in the semiconductor substrate is provided in the semiconductor chip, and when the channel region is conductive, the piezoelectric thin film is connected to one end of the channel region so that the conductive state of the channel region is changed due to the charge according to the induces charge amount flows through the channel region.

Preferably, in the acoustic sensor, a piezoelectric thin film is divided in a plurality of blocks to be arranged at least in one direction, and semiconductor chips outputs signals individually or in block units.

Preferably, in the acoustic sensor, the piezoelectric thin film is formed of a ferroelectric material, and is formed so that a coercive electric voltage which reverses polarization of the piezoelectric thin film is smaller than a withhold voltage of the semiconductor chip.

Preferably, the ultrasound probe includes the above acoustic sensor.

An ultrasound diagnosis apparatus includes the ultrasound probe, a signal processor which analyzes signals relating to ultrasound waves received by the ultrasound probe, and an output unit which outputs analysis results of the signal processor in a predetermined format.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 4A is a view used to explain a charge conveyance procedure carried out by a CCD;

FIG. 4B is a view used to explain the charge conveyance procedure carried out by the CCD;

FIG. 4C is a view used to explain the charge conveyance procedure carried out by the CCD;

FIG. 4D is a view for explaining the charge carrying procedure carried out by the CCD;

FIG. 6A is a block diagram showing an inner structure of an ultrasound probe of the second embodiment;

FIG. 6B is a cross-sectional view used to explain a phasing adder of the second embodiment;

DESCRIPTION OF THE PREFERRED EMBODIMENTS

Hereinafter, embodiments of the present invention will be described with reference to the drawings.

First Embodiment

Figure 1:
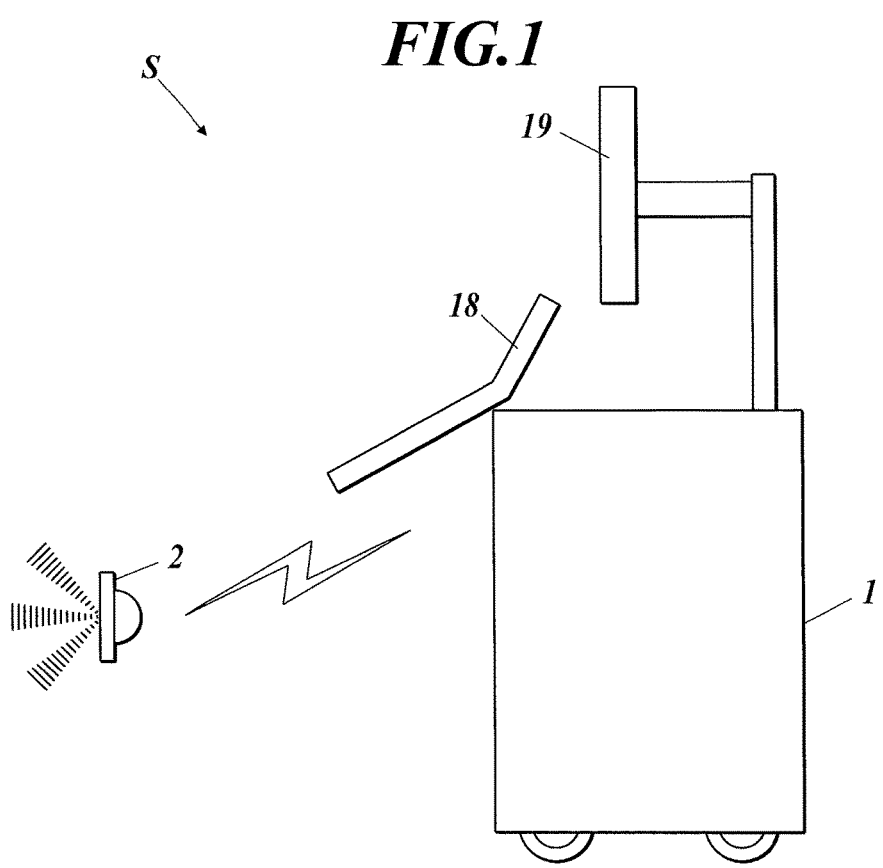
FIG. 1 is an overall view of an ultrasound diagnosis apparatus including an ultrasound probe of an embodiment of the present invention.

FIG. 1 is a view showing an overall structure of an ultrasound diagnosis apparatus S including an ultrasound probe 2 of the first embodiment.

The ultrasound diagnosis apparatus S includes a main body 1 and the ultrasound probe 2. The main body 1 includes an operation input unit 18, an output display unit 19, a controller (not shown) and a communication unit (not shown). The controller of the main body 1 outputs a control signal to the ultrasound probe 2 via the communication unit to make the ultrasound probe 2 output ultrasound waves on the basis of external input operations to input devices such as a keyboard and mouse of the operation input unit 18. Further, the controller of the main body 1 receives input detection data of ultrasound waves from the ultrasound probe, performs various processes on the received input detection data and displays the results in a liquid crystal screen or the like of the output display unit 19 as needed.

The ultrasound probe 2 transmits ultrasound waves (here, about 1 to 30 MHz) to a subject and receives reflected waves (echo) which are the waves among the transmitted ultrasound waves that reflected off the subject. The ultrasound probe 2 performs receiving and sending of control signals and data with the main body 1 through a wireless communication.

Figure 2:
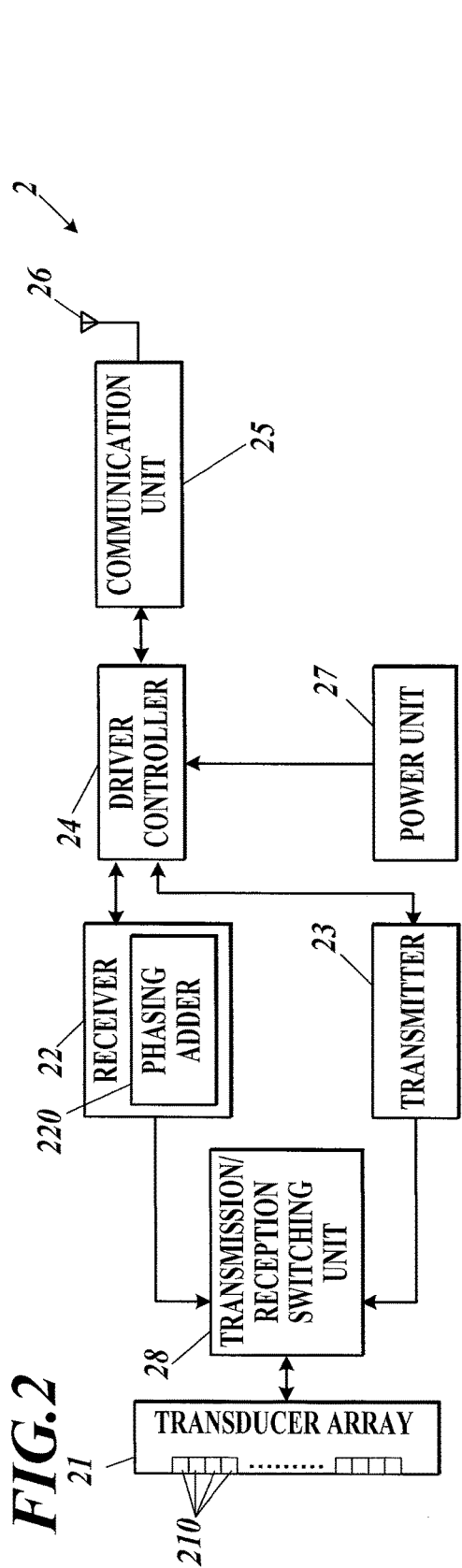
FIG. 2 is a block diagram showing an inner structure of the ultrasound probe.

FIG. 2 is a block diagram showing an inner structure of the ultrasound probe 2.

The ultrasound probe 2 includes a transducer array 21, a receiver 22, a transmitter 23 (transmission drive unit), a drive controller 24 (capacity controller), a communication unit 25 (signal output unit, wireless communication unit), antenna 26, power unit 27, transmission/reception switching unit 28 (transmission/reception switching drive unit), etc.

The transducer array 21 is an array of a plurality of transducers 210, each transducer including a piezoelectric device formed of a piezoelectric element having electrodes respectively on both ends thereof where charges appear due to deformation (expansion and contraction) of the piezoelectric element. These transducers 210 are, for example, arranged in one-dimensional array in a predetermined direction. Due to a voltage pulse (pulse signal) being applied to each transducer 210, its piezoelectric element deforms, and an ultrasound wave having an amplitude according to the degree of the voltage is transmitted. Further, when an ultrasound wave of a predetermined frequency band is transmitted to each transducer 210, the thickness of the piezoelectric element varies (vibrates) due to the sound pressure of the ultrasound wave and a charge according to the varying degree appears, and charges in amounts according to the charge are induced in the electrodes at both ends of the piezoelectric device.

As for the piezoelectric material used for the piezoelectric element of each transducer 210, for example, PZT (lead zirconate titanate) is suggested. Alternatively, any of other various piezoelectric material such as LiNb3, LiTaO3, KNbO3 and crystal which are single crystals, Pb(Mg⅓Nb⅔)O3 and (Pb, Sm)Ti3 which are polycrystal, PMN-PT (lead-magnesium niobate-titanate) and PZN-PT (lead zinc niobate-titanate) which are relaxor ferroelectric, PVDF (polyvinylidene fluoride) or PVDF copolymer which are organic material, polyvinylidene cyanide or vinylidene cyanide copolymer, nylons of odd numbers such as nylon 9 and nylon 11, aromatic nylone, alicyclic nylon, polyaclic acid, polyhydroxy carboxylic acid such as PHB (polyhydoxy butyric acid), sellylose derivative, polyurea, etc. cab be used. Further, a composite material where an inorganic piezoelectric material and an organic piezoelectric material are combined can also be used.

Among the above, specifically, a ferroelectric material such as PZT is preferably used as the piezoelectric material With respect to the ultrasound probe 2 of the embodiment, for example, 192 transducers 210 are included in the transducer array 21. Alternatively, the transducers 210 may be arranged in a two dimensional array and may obtain a three dimensional ultrasound image. The number of transducers 210 can be set appropriately according to various conditions such as resolution, power consumption, data transmission speed, etc. The ultrasound probe 2 may be an electronic scanning type or a mechanical scanning type. As for the scanning method, any of the linear scanning, sector scanning and convex scanning can be adapted. The receiving band width of the ultrasound waves in the ultrasound probe 2 is appropriately set.

The ultrasound diagnosis apparatus S is configured so as to be able to use any one of different ultrasound probes 2 according to the subject to be inspected in combination with the main body 1.

The receiver 22 converts the charges which are induced with input of ultrasound waves in respective transducers 210 of the transducer array 21 into voltage signals according to the charge amounts and amplifies the voltage signals. Then, the receiver 22 outputs data obtained by converting the voltage signals into digital data at a predetermined sampling frequency as received signals. The receiver 22 includes a phasing adder 220, a LNA (Low Noise Amplifier) 223 (signal amplifier), an ADC (analog/digital converter) 224, etc. (see FIG. 5). The receiver 22 will be describer later.

The transmitter 23 outputs voltage pulse signals to certain transducers 210, the voltage pulse signals are for making the transducers 210 output ultrasound waves of predetermined amplitude and frequency, the transducers 210 being specified according to the control signals from the drive controller 24.

The transmission/reception switching unit 28 connects the transducer array 21 with either of the transmitter 23 and the receiver 22 on the basis of a control signal from the drive controller 24 so as to make the transmitter 23 transmit voltage pulse signals relating to driving of the transducers 210 or to transmit the electric signals relating to the ultrasound waves which are input to the transducers 210 to the receiver 22.

The drive controller 24 sends a control signal to the transmission/reception switching unit 28 according to the control signal input from the communication unit 25 to switch the connection of the transducer array 21 to either of the transmitter 23 and the receiver 22, the drive controller 24 operates the transmitter 23 to make the ultrasound waves be output from individual transducers 210. Further, while the ultrasound waves are being output, the drive controller 24 makes the transducer array 21 output the charge signals according to the ultrasound waves input to individual transducers 210 to the receiver 22 and obtains the received signals from the receiver 22. Moreover, the drive controller 24 transmits the received signals of the ultrasound waves to the main body 1 from the communication unit 25 and the antenna 26.

The communication unit 25 is a communication interface for carrying out sending and receiving of control signals and obtained data with the main body 1. As for such communication interface, any one of various well-known wireless communication methods can be adapted. As for such wireless communication methods, communication formats whose data transfer speed to the main body 1 from the ultrasound probe 2 is satisfactorily fast such as communication through a wireless LAN (IEEE802.11n, etc.), Bluetooth (registered trademark) or the like, communication methods using frequency bands based on body area network (BAN; IEEE802.15.6) are suggested.

The antenna 26 is for sending and receiving communication radio waves when the communication unit 25 carries out wireless communication with the communication unit of the main body 1. As for the antenna 26, an antenna having an appropriate size and shape according to the communication frequency and the size of the ultrasound probe 2 is used.

The power unit 27 is for supplying power to various parts of the ultrasound probe 2 and operating them. Although the power unit 27 is not specifically limited, it usually include a dry-cell battery. The power unit 27 also includes a booster circuit and may boost the output voltage from the battery such as the dry-cell battery to an appropriate voltage according to the ultrasound waves output from the transducers 210 and then, may supply power to the transducers 210.

Next, the configuration and operation relating to ultrasound wave reception in the ultrasound probe 2 of the embodiment will be described.

Figure 3:
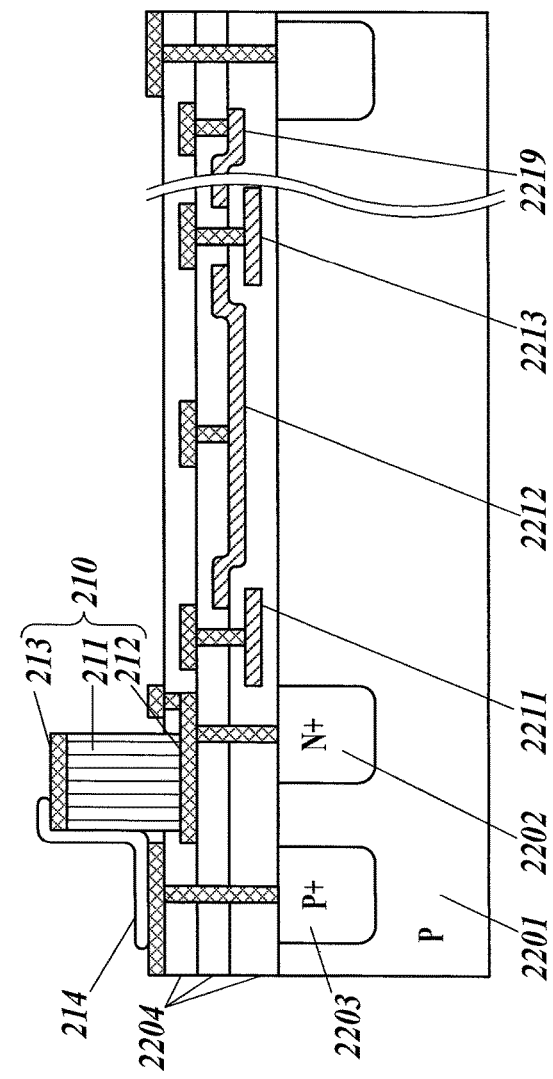
FIG. 3 is a cross-sectional view used to explain a phasing adder.

FIG. 3 is a cross-sectional view used to explain the structure of an ultrasound wave reception part in the ultrasound probe 2 of the embodiment. The cross-sectional view shows the cross-section of the semiconductor substrate 2201 including one transducer 210 and its corresponding CCD 221.

In the ultrasound probe 2 of the embodiment, the transducers 210 (piezoelectric devices) are arranged and formed integrally with the semiconductor substrate 2201, each transducer 210 including a piezoelectric element 211 and electrodes 212 and 213 at both sides of the piezoelectric element 211. Here, the semiconductor substrate 2201 is a p-type substrate. The electrode 212 is connected with an n-type region 2202 that is provided on one side (upper side) of the semiconductor substrate 2201. Further, the electrode 213 is connected with the semiconductor substrate 2201 via the conductive member 214. This connection part is a p-type region 2203 whose impurity concentration is increased by injecting impurity ion such as B (boracic acid) so that the current flows between the conductive member 214 and the semiconductor substrate 2201. Further, an ohmic contact is formed between the connection part and the metallic conductive member 214.

Preferably, the electrodes 212 and 213 are conductive bodies with small electric resistance and for example, aluminum is used for the electrodes 212 and 213. The congealing point of aluminum under normal atmospheric pressure is about 660 degrees. The semiconductor chip used for drive control in the ultrasound probe 2 of the embodiment is formed by individual circuit boards (circuits), electrodes, a transducer 210 being laminated in this sequence on the semiconductor substrate 2201. Therefore, the heat balance in the later procedure affects the part formed in earlier procedure. That is, in a case where the transducer 210 is further laminated after a circuit is formed on the semiconductor substrate 2201, the piezoelectric phase of the piezoelectric material (ferroelectric phase in a case of ferroelectrics) needs to be generates at a temperature below the above temperature of congealing point (for example, 650 degrees).

The semiconductor substrate 2201 which is the p-type substrate and the n-type region 2202 forms a p-n junction and has a diode structure. The n-type region 2202 is a conductive region where impurity ion such as P (phosphorus), As (arsenic), etc. is injected. The n-type region 2202 is grounded or is connected to a predetermined external voltage source (Vdd). When the transducer 210 is deformed by the incident ultrasound wave and a charge appears, charges of opposite polarity are respectively induces in the electrodes 212 aiesd 213.

Insulating layers 2204 are provided on the semiconductor substrate 2201, and a plurality of electrodes are arranged in the insulating layers 2204. These electrodes include an IG (input gate) electrode 2211 adjacent to the n-type region 2202, a plurality of transfer electrodes (although two transfer electrodes 2212 and 2213 are shown here, the number is not limited to two) and an OG (output gate) electrode 2219. The CCD (Charge Coupled Device) 221 (delay charge transfer unit) is formed of the electrodes, the channel region in the semiconductor substrate 2201 under the electrodes, and the n-type region 2202. Signal charge (electrons) according to the charges induced in the electrodes 212 and 213 is introduced in to the n-type region 2202, transferred to the potential wells (charge holding units) formed at the channel region below the electrodes according to the voltages applied to the individual electrodes over a plurality of steps in an order, and sent to the adder 222 (delay adder). Here, the area of the lower surface of the first transfer electrode 2212 is larger than the areas of the lower surfaces of the transfer electrode 2213 and the transfer electrodes thereafter which are arranged between the transfer electrode 2212 and the OG electrode 2219. That is, the capacity of the potential well that is generated in the channel region of the transfer electrode 2212 is greater than the capacity of the potential well that is generated in the channel region of each of the transfer electrode 2213 and transfer electrodes thereafter.

FIGS. 4A to 4D are diagrams used to explain a charge conveyance operation by the CCD 221. With respect to each of the positions (horizontal axis) corresponding to the electrodes, the vertical axis indicates the potential in the semiconductor substrate 2201 under the corresponding electrode.

In the ultrasound probe 2 of the embodiment, when each transducer 210 receives an ultrasound wave, the voltage VIG applied to the IG electrode 2211 and the voltage Vϕ1 applied to the first transfer electrode 2212 are switched to ON voltage, a potential well is formed in the channel regions of these electrodes, a charge (electrons) is accumulated in the n-type region 2202 and the potential well is formed continuously from the n-type region 2202 (a1, the shaded part) as shown in FIG. 4A. The impedance of the transducer 210 (piezoelectric element 211) in the size required for receiving an ultrasound wave is smaller than the impedance according to the capacity of the n-type region 2202 which is the region where the charge amount according to the charge that occurs at the electrode 212 of the transducer 210 is input. Therefore, the charge obtaining efficiency is low if only the n-type region 2202 is used. In view of this, when an ultrasound wave is to be received, ON voltage is applied to the IG electrode 2211 and the transfer electrode 2212 to make the potential well formed in the channel regions under these electrodes and the n-type region 2202 be electrically connected to form a larger charge accumulation region (first holding unit) and increase the electric capacity to lower the impedance of the charge accumulation region. Thereby, improve the impedance matching with the transducer 210 and increase charge obtaining efficiency.

When ending the charge accumulation that goes along with ultrasound wave reception by the transducer 210, the voltage VIG that is applied to the IG electrode 2211 is switched to OFF voltage from ON voltage, the potential well formed in the channel region of the IG electrode 2211 disappears and the N type region 2202 and the potential well under the transfer electrode 2212 are cut off as shown in FIG. 4B. Next, the voltage Vϕ2 that is applied to the transfer electrode 2213 is switched to ON voltage and the potential well b1 below the transfer electrode 2212 expands to the channel region below the transfer electrode 2213.

Thereafter, as shown in FIG. 4C, the potential well below the transfer electrode 2212 disappears by the voltage Vϕ1 applied to the transfer electrode 2212 being switched to OFF voltage. Thereby, the potential well that included the region below the transfer electrode 2212 is limited to the channel region part c1 below the transfer electrode 2213 having a small area (capacity), and the signal charge is converged to this potential well.

Finally, by the voltage VOG applied to the OG electrode 2219 being switched to ON voltage in a state where the potential well is formed below the transfer electrode adjacent to the OG electrode 2219 and the signal charge is accumulated therein, the signal charge flow in to the connected adder through the channel region d1 below the OG electrode 2219, as shown in FIG. 4D.

In such way, after the charge according to the expansion and contraction of the transducer 210 is once obtained, the signal charge is converged in the potential well (the holding unit of later stage) whose capacity is smaller than that of the above charge accumulation region in the CCD 221. Thereby, power consumption relating to voltage application to transfer electrodes (for example, due to current leakage) can be reduced and there is no need to make the area of the CCD 221 be larger than necessary.

Figure 5:
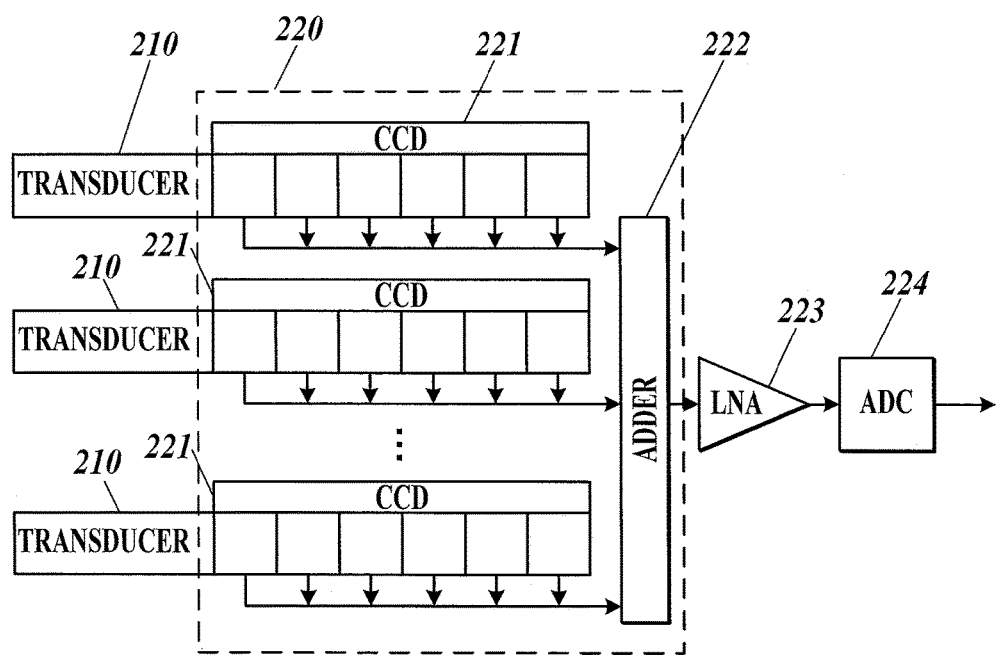
FIG. 5 is a diagram used to explain a receiver.

FIG. 5 is a diagram used to explain the receiver 22.

The receiver 22 includes the phasing adder 220, a LNA 223 and an ADC 224.

The phasing adder 220 includes a plurality of CCDs 221 which transfer the charges obtained from respective transducers 210 and an adder 222 which adds the charge amounts transferred from the individual CCDs 221 (phasing addition), the electric charge being transferred over the course of a predetermined number of stages in each CCD. The added charge obtained by the charge amounts being added by the phasing adder 220 is converted into a voltage value (for example, floating diffusion), amplified in the LNA 223, output to the ADC 224 and converted into a digital value at a predetermined sampling frequency.

As shown in FIG. 3, FIGS. 4A to 4D, in the phasing adder 220 of the embodiment, the charge in the amount corresponding to the charges that are induced in the electrodes 212 and 213 at both ends in response to the deformation of each transducer 210 is taken in directly to the corresponding CCD 221 from the n-type region 2202 without being amplified. The charge which is taken in is transferred from a potential well to another potential well over a plurality of potential wells formed in the CCD 221 at a predetermined time interval. Then, after a number of transferring which is set according to the delay time, the charge is selectively read out from any of the potential wells. That is, in the phasing adder 220, by setting the position of the potential well from which the charge amount is to be read out for each CCD 221, the transfer stages relating to phasing addition, that is, the number of times of transferring (the number of delay steps) is set individually.

In FIG. 3 and FIGS. 4A to 4D, a case where the signal charge is directly read out from the potential well below the transfer electrode 2213 via the channel region below the OG electrode 2219 is shown. However, the charge amounts held in individual potential wells formed by the voltages being applied to the intervening transfer electrodes can be selectively read out. Although it is not limited, in such reading out, the charge amount is read out by non-destructive mirroring and not by directly taking out the charge held in the potential wells. By having such configuration, same data can be read out for a plurality of times from a plurality of potential wells with different number of delay steps (delay time). In such case, the signal charge that is transferred to the potential well which is the last transfer electrode in the CCD 221 can similarly be read out in a non-destructive manner and not by directly taking it out and can be released by being grounded to the substrate according to the voltage VOG applied to the OG electrode.

Here, the number of potential wells that can be formed in the CCD 221, that is, the maximum number of delay steps can be arbitrarily set. However, as the number increases, the loss in charge and the power needed for transferring increase. Thus, it is preferred to curb the number of the potential wells as much as possible (for example, 10 steps or less).

The charges read out from the plurality of CCD 221 corresponding to one adder 222 are added in the adder 222. The result charge amount is amplified by the LNA 223 after being converted into a voltage value. That is, each piece of data obtained from a plurality of transducers 210 are not individually amplified, instead they are added and then the result thereof is amplified only once.

As described above, the phasing adder 220 according to the ultrasound probe 2 of the first embodiment includes a plurality of CCDs 221 and an adder 222. Each CCD 221 includes a n-type region 2202 and a channel region, and each CCD 221 obtains a signal charge amount, which is not amplified, in response to the charge generated in its corresponding transducer 210 including a piezoelectric element 211 which causes a charge in response to the sound pressure of the input ultrasound wave and performs sending and receiving of the signal charge over the course of a set number of stages while holding the signal charge for a predetermined time at each stage. The adder 222 performs phasing addition of the signal charges which are transferred over the course of the set number of stages while being held at each stage in each CCD 221.

In the phasing adder 220, with respect to each CCD 221, the electric capacity of the charge accumulation region where the signal charge obtained at the time of ultrasound wave reception, which includes the n-type region 2202 and the first stage among the plurality of stages of the channel region, is greater than the electric capacity of each of the potential wells which holds the signal charge at the second stage and the staged thereafter. Since the impedances of the transducer 210 and the charge accumulation region are matched while curbing the number of LNA 223 and controlling the power consumption, signals can be obtained efficiently and appropriately from the received ultrasound wave while maintaining SNR.

In each CCD 221, the individual potential wells which hold the signals in the second stage and the stages thereafter have the same capacity. Therefore, the potential wells can be formed easily in the minimum size required for charge transferring which prevents increase in size and increase in power consumption. Further, by forming the potential wells in the minimum size, the time required for signal charge transfer can be prevented from increasing.

Since each CCD 221 is formed on a semiconductor chip substrate by being integrally connected with the piezoelectric element 211, a compact phasing adder 220 can be obtained quickly in one easy manufacturing process.

Since the charge transfer is performed by a CCD 221, the signal charge can be transferred from a potential well to another potential well having different impedances in a simple configuration and by a simple process.

The ultrasound probe 2 of the embodiment includes the phasing adder 220, the transducers 210, the LNA 223 which amplifies the voltage signal corresponding to the charge amounts obtained in the phasing adder 220 and a communication unit 25 which outputs the amplified voltage signal to the main body 1.

Therefore, by curbing the number of LNA 223, power consumption in the ultrasound probe 2 can be reduced, the duration time of the battery can be improved and heat generation in the ultrasound probe 2 can be reduced so that the ultrasound probe 2 can be used on a subject such as a human body that has limited tolerance to heat. Further, since data is output from the communication unit 25 after being subjected to processes such as phasing addition and the like, the communication volume between the ultrasound probe 2 and the main body 1 can be reduced.

Moreover, since the communication unit 25 outputs data to the main body 1 through wireless communication, a user can easily perform the operation of a wireless ultrasound probe 2 relating to ultrasound diagnosis.

Further, the ultrasound probe 2 of the embodiment includes the transmitter 24 which outputs ultrasound waves from the transducers 210 and the transmitter 23, and transmission and reception of ultrasound waves can be caused by the transmission/reception switching unit 28 which makes the receiver 22 and the transmitter 23 be connected with the transducers 210 alternately according to the control signal.

Second Embodiment

Next, an ultrasound probe and a phasing adder according to the second embodiment will be described.

FIG. 6A is a block diagram showing an inner structure of the ultrasound probe 2 of the embodiment. FIG. 6B is a cross-sectional view used to explain the phasing adder 220b.

As shown in FIG. 6A, the ultrasound probe 2 of the second embodiment has the configuration same as that of the ultrasound probe 2 of the first embodiment except for the configuration of the phasing adder 200b being different from that of the phasing adder 220 of the ultrasound probe 2 of the first embodiment. Therefore, the same reference numerals are used for the same parts and their explanation is omitted.

As shown in FIG. 6B, with respect to each CCD in the phasing adder 220b of the ultrasound probe 2 of the second embodiment, a plurality of transfer electrodes are arranged between the IG electrode 2211 and the OG electrode 2219, the areas of the sides of the transfer electrodes that face the semiconductor substrate 2201 being approximately the same. Although transfer electrodes 2212b to 2215b are shown in the drawing, the number of transfer electrodes are not limited to the number of the transfer electrodes shown in the drawing.

FIGS. 7A to 7D are diagrams used to explain the charge transfer operation performed by CCDs of the phasing adder 220b of the embodiment. Here, a case where six transfer electrodes are arranged between the IG electrode 2211 and the OG electrodes 2219 and the ON/OFF voltage supplied to the transfer electrodes can be switched independently will be described.

Figure 7A:
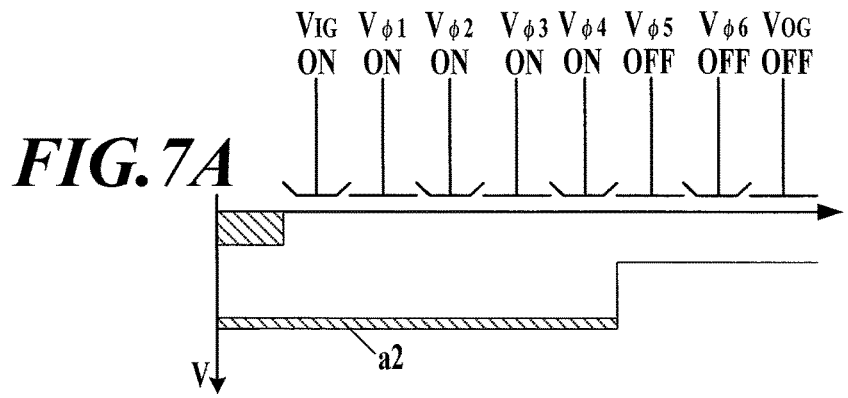
FIG. 7A is a diagram used to explain a charge conveyance procedure carried out by a CCD relating to the ultrasound probe of the second embodiment.

In each CCD of the phasing adder 220b of the embodiment, at the time of ultrasound wave reception, all of the voltage $V\phi 1$ to $V\phi 4$ applied to the transfer electrodes 2212b to 215b, respectively, are switched to ON voltage. Thereby, a potential well is continuously formed across the N type region 2202 and the channel regions below the electrodes to which ON voltage is applied as shown in FIG. 7A, this potential well is the charge accumulation region a2. In such way, the electric capacity of the charge accumulation region increases and the impedance of the phasing adder 220b is reduced improving the matching to the impedance of the transducer 210 (piezoelectric element 211).

Figure 7B:
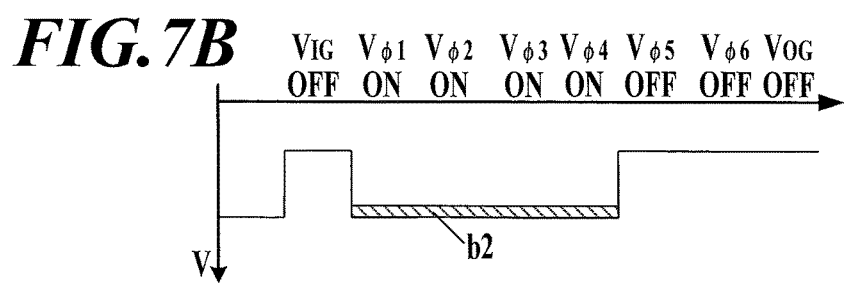
FIG. 7B is a diagram used to explain the charge conveyance procedure carried out by the CCD relating to the ultrasound probe of the second embodiment.
Figure 7C:
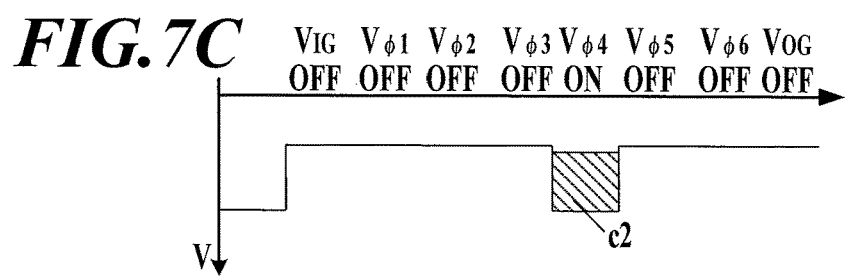
FIG. 7C is a diagram used to explain the charge conveyance procedure carried out by the CCD relating to the ultrasound probe of the second embodiment.

When the time period during which ultrasound waves are received ends, as shown in FIG. 7B, the voltage applied to the IG electrode 2211 is switched to OFF voltage and the potential well b2 below the transfer electrodes is cut off from the n-type region 2202. Further, the voltage applied to the transfer electrodes is switched to OFF voltage in an order starting from the transfer electrode nearest to the IG electrode 2211. Then, as shown in FIG. 7C, in a state where only the voltage $V\phi 4$ applied to the fourth transfer electrode 2215b is ON voltage, the accumulated signal charge is converged at the potential well c2 that is formed in the channel region below the transfer electrode 2215b.

Figure 7D:
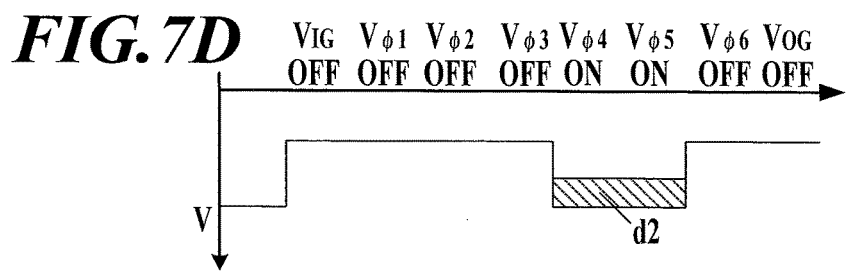
FIG. 7D is a diagram used to explain the charge conveyance procedure carried out by the CCD relating to the ultrasound probe of the second embodiment.
Figure 7E:
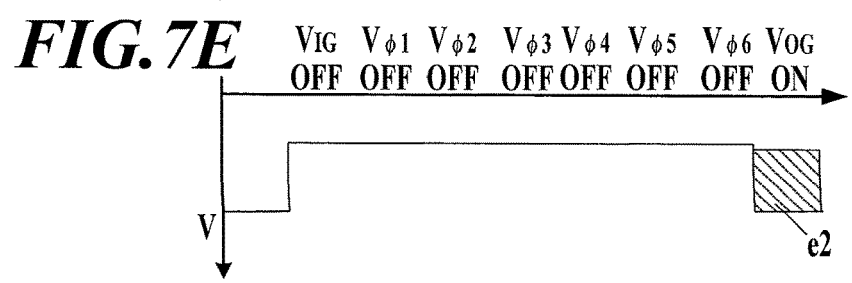
FIG. 7E is a diagram used to explain the charge conveyance procedure carried out by the CCD relating to the ultrasound probe of the second embodiment.

Thereafter, as shown in FIG. 7D, the voltage (here, $V\phi 5$) applied to the transfer electrode that is adjacent to the transfer electrode (here, the transfer electrode 2215b) on the OG electrode 2219 side, this electrode corresponding to the potential well where the charge is accumulated, is switched to ON voltage, the signal charge flows into the potential well below the adjacent transfer electrode forming the charge accumulation region d2, and the voltage (here, $V\phi 4$) applied to the transfer electrode 2215b corresponding to the previous potential well is switched to OFF voltage so that the signal charge moves toward the OG electrode 2219. Due to such process being repeated in an order, at the end, the signal charge is sent directly to the adder 222 via the channel region e2 below the OG electrode 2219 or is sent to the adder 222 by being indirectly read out and then is released to the ground as shown in FIG. 7E.

Figure 8A:
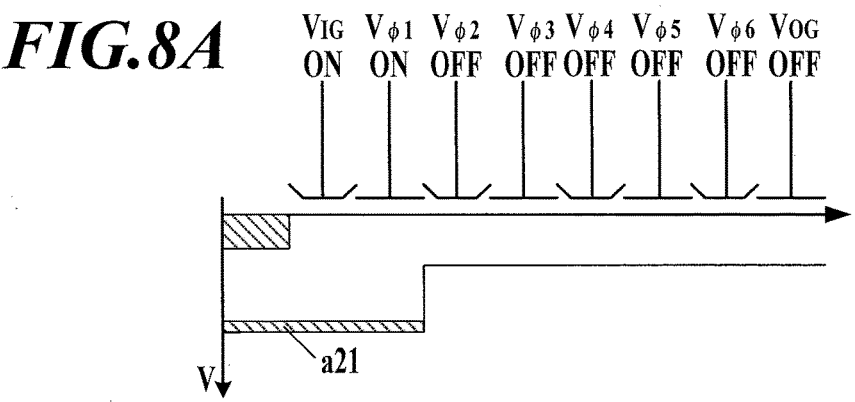
FIG. 8A is a diagram used to explain the setting of a charge accumulation region at the time of ultrasound wave reception.
Figure 8B:
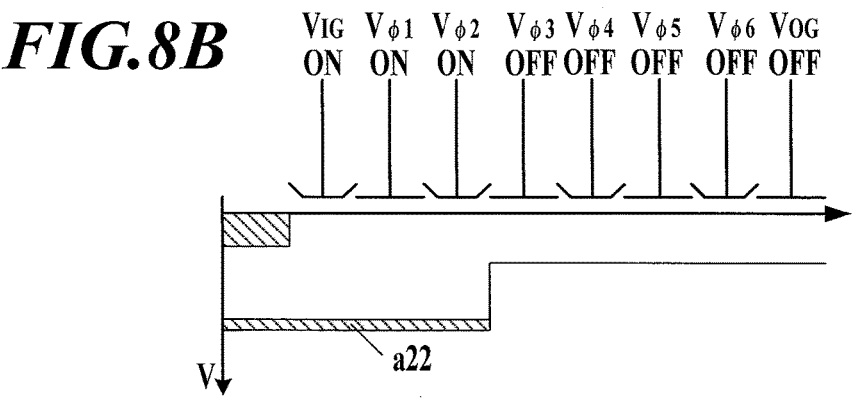
FIG. 8B is a diagram used to explain the setting of the charge accumulation region at the time of ultrasound wave reception.
Figure 8C:
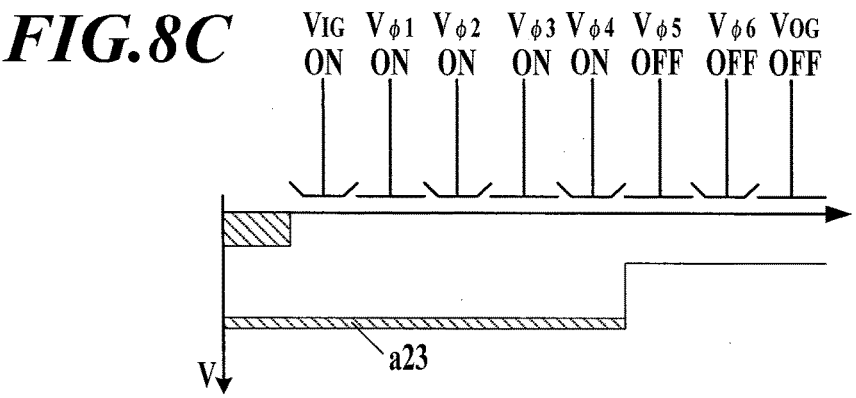
FIG. 8C is a diagram used to explain the setting of the charge accumulation region at the time of ultrasound wave reception.

FIGS. 8A to 8C are diagrams used to explain the setting of the charge accumulation region at the time of ultrasound wave reception.

In the receiver 22 of the ultrasound probe 2 of the embodiment, the number of transfer electrodes to which ON voltage is applied at the time of ultrasound wave reception can be changed. The ultrasound waves are transmitted and output from the transducers 210 in response to application of voltage pulses, and thereafter, the ultrasound waves are received after a time period according to the distance to the subject on which the ultrasound waves reflect off has elapsed. Therefore, in a case where the distance to the subject is short, the reflected ultrasound waves are received in a short time period after the ultrasound waves are output and in a case where the distance to the subject is long, the reflected ultrasound waves from the far subject are received after a time period longer than the time period waited before the receiving timing of the ultrasound waves which reflected off the close subject has elapsed. At this time, since the ultrasound waves are spatially diffused and transmitted, the reflected ultrasound waves reflected off the far subject has low received signal strength in average comparing to the reflected ultrasound waves reflected off the close subject.

In view of the above, in the ultrasound probe 2, the drive controller 24 controls so as to reduce the number of transfer electrodes to which On voltage is applied in the receiver 22 right after the ultrasound waves are transmitted as shown in FIG. 8A. Here, the applied voltages $V\phi 1$ to $V\phi 6$ are set and controlled so that On voltage is only applied to the first transfer electrode adjacent to the IG electrode 2211. Thereafter, after a predetermined time has elapsed since transmission of ultrasound waves, the number of transfer electrodes to which ON voltage is applied is increased as shown in FIG. 8B. Here, the applied voltage $V\phi 2$ which is supplied to the second transfer electrode is changed to ON voltage and the charge accumulation region (potential well) a22 is expanded. If a predetermined time has further elapsed since transmission of ultrasound waves, the number of transfer electrodes to which ON voltage is applied is further increased as shown in FIG. 8C. Here, the applied voltages $V\phi 1$ to $V\phi 4$ which is applied to the four transfer electrodes adjacent to each other are ON voltage, and the charge accumulation region (potential well) a23 is further expanded.

That is, when receiving strong reflected ultrasounds from a close distance, the number of transfer electrode which are to be turned on is reduced to decrease the electric capacity and the best impedance matching possible in the receiver 22 is not carried out to cause mismatch in impedances at a certain level intentionally to reduce the reception efficiency. On the other hand, when receiving the reflected ultrasound waves from a long distance, the number of transfer electrodes to be turned on is increased to increase the electric capacity and the impedance is better matched to the transducers 210 so that the charge corresponding to the intensity of the ultrasound waves which are efficiently received is obtained. Within the range of the number of transfer electrodes to which ON voltage can be applied at the same time in the receiver 22, the reception efficiency is normally determined according to the number of transfer electrodes that are turned on. Therefore, the amplification factor by which the voltage according to the charge amounts obtained by the addition in the phasing adder 220b is to be amplified in the LNA are independently adjusted according to the number of transfer electrodes which are turned on so that the voltages are returned to voltages of a constant reception level.

In a case where the charge accumulation region is large, the voltage VIG applied to the IG electrode 2211 is switched to OFF voltage and then, the signal charge is transferred and read out after the potential well is reduced. Therefore, the minimum time needed until reading-out from the start of ultrasound wave reception increases. Therefore, the receiving intervals of ultrasound waves need to be decided according to the maximum range of the set charge accumulation region.

As described above, each CCD of the phasing adder 220b in the ultrasound probe 2 of the second embodiment includes a plurality of transfer electrodes (2212b to 2215b), and the number of transfer electrodes to which ON voltage is applied with the IG electrode 2211 at the time of ultrasound wave reception is changed to form a continuous charge accumulation region and set the electric capacity of the charge accumulation region. Therefore, the impedances between the transducer 210 and the charge accumulation region can be matched easily and efficiently without greatly changing the configuration of the CCDs 221, and charge corresponding to the ultrasound wave intensity can be obtained efficiently.

The number of potential wells that can be formed in the channel regions of the semiconductor substrate 2201 corresponds to the maximum number of steps of delay transferring carried out by using each CCD 221 according to the number of transfer electrodes used for forming of the above mentioned large charge accumulation region. Therefore, the size of the charge accumulation region can be changed flexibly as needed to change the electric capacity.

The transfer electrodes are provided so that the electric capacities of the potential wells are the same. Therefore, the semiconductor chips provided with such CCDs 221 can be manufactured easily. Further, the electric capacities of the charge accumulation regions can be set with an appropriate capacity intervals and transmission of the signal charges can be performed at an appropriate speed while limiting the sizes to the minimum size.

Further, by setting the electric capacity of the electric accumulation regions individually for each corresponding transducer 210, the matching level of the impedances of the transducer 210 and its corresponding charge accumulation region can be changed to perform weighting of receiving sensitivity according to the direction the ultrasound waves, which are the detection target, are received, and the position of a transducer 210 in the plurality of transducers 210 which is used for reception. Further, by similarly changing the matching level of the impedances according to the received signal strength of the ultrasound waves, that is, according to the distance to a subject on which the ultrasound waves are reflected off, dynamic range that is wider or equal to the received signal strength width of the transducer 210 can be realized.

The ultrasound probe 2 includes the drive controller 24, and the size of the electricity accumulation regions can be set sequentially. Therefore, the level of impedance matching can be changed finely during reception and the above mentioned spatial weighting of receiving sensitivity and expansion of dynamic range can be carried out.

By the drive controller 24 changing the level of impedance matching according to the time elapsed since the start of ultrasound wave reception, the charge corresponding to the strength of the ultrasound waves received with the efficiency according to the distance from the subject can be obtained. Therefore, received data having wide dynamic range can be obtained with reception efficiency according to the received signal strength of the ultrasound waves can be obtained easily and in line with the reality of ultrasound diagnosis, and more accurate ultrasound diagnosis can be performed.

Third Embodiment

Next, the ultrasound probe 2 of the third embodiment will be described.

Figure 9A:
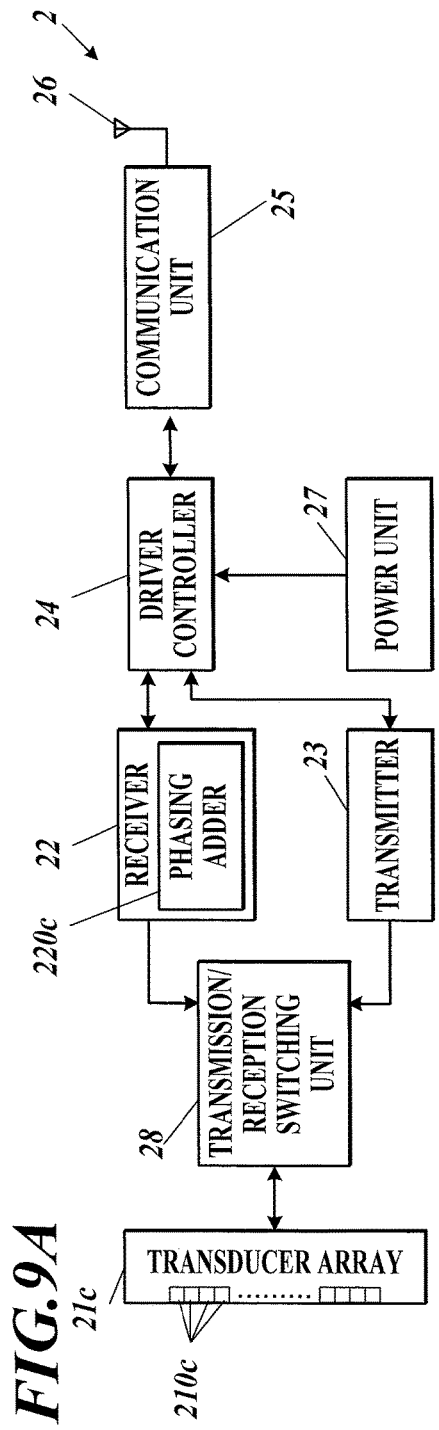
FIG. 9A is a block diagram showing an inner structure of an ultrasound probe of the third embodiment.
Figure 9B:
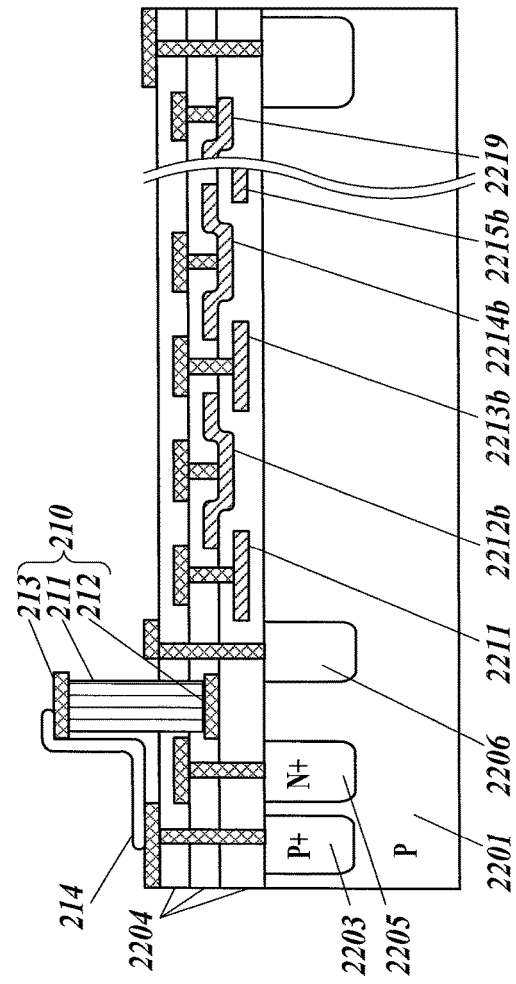
FIG. 9B is a cross-sectional view used to explain a phasing adder of the third embodiment.

FIG. 9A is a block diagram showing the inner structure of the ultrasound probe 2 of the embodiment. FIG. 9B is a cross-sectional view used to explain the phasing adder 220c of the ultrasound probe 2.

As shown in FIG. 9A, the ultrasound probe 2 of the third embodiment has the configuration same as that of the ultrasound probes of the first embodiment and the second embodiment except for the inner structure of the phasing adder 220c being different. Therefore, the same reference numerals are used for the same parts and their description is omitted.

With respect to each CCD in the phasing adder 220c of the embodiment, two n-type regions 2205 and 2206 are not directly connected to the electrode 212 of the transducer 210 and the potential according to the charge of the electrode 212 is to be generated in the channel region between the n-type regions 2205 and 2206 as shown in FIG. 9B. The n-type region 2205 is, for example, connected to a predetermined voltage source, and in a case where a predetermined potential is applied to the channel region below the electrode 212 causing the electrode 212 be energized, current flows to the n-type region 2206 from the n-type region 2205. The configurations other than the above configuration are the same as those of the phasing adder 220b of the ultrasound probe 2 of the second embodiment. Therefore, the same reference numerals are used for the same parts and their description is omitted.

That is, since the configuration is similar to that of MOSFET, in each CCD in the phasing adder 220c of the embodiment, the transducer 210 is provided very near (here, right above) the channel region between the n-type regions 2205 and 2206 in order to efficiently introduce the signal charge to the CCD 221. Therefore, the insulating layer 2204 between the electrode 212 and the channel region is preferably thin within the range a problematic current leak does not occur.

Even in such configuration, due to ON voltage being applied to the IG electrode 2211 and a predetermined number of transfer electrodes adjacent to the IG electrode 2211 to form a continuous charge accumulation region at the time of ultrasound wave reception, the charge according to the reception level of the ultrasound waves can be lead to the CCD 221 at an appropriate impedance to be obtained.

As described above, each CCD of the phasing adder 220c of the ultrasound probe 2 of the third embodiment is formed on the semiconductor substrate 2201 integrally with the transducer 210 by the manufacturing process which is the same as that of MOSFET. Since the electrode 212 is provided very close to the channel region between the n-type regions 2205 and 2206, ultrasound waves can be received with high sensitivity by a simple manufacturing method.

The present invention is not limited to the above embodiments, and various modifications can be carried out.

For example, in the first to third embodiments, the next reception of ultrasound waves is not performed until the charge relating to the previously received ultrasound waves is discharged via the channel region below the OG electrode 2219. However, after the charge is discharged from the transfer electrodes which are turned on during reception of the ultrasound waves, that is, from the charge accumulation region and the channel region (potential well) below the transfer electrodes adjacent to the charge accumulation region, the next reception of ultrasound waves can be started.

Further, in the first embodiment, the description is given by taking the transfer electrode 2212 which is elongated in the transferring direction of the signal charge as an example.

However, the size and shape of the expanded transfer electrode is not limited to the above example. That is, the transfer electrode 2212 may be formed so as to be elongated in the direction perpendicular to the transferring direction of the signal charge and further, may be formed so as to be extended in both the transferring direction and the direction perpendicular to the transferring direction. That is, the shape of the transfer electrode can be changed in two dimensions.

Furthermore, a plurality of transfer electrodes may be provided perpendicularly to the transferring direction of the signal charge, and OFF voltage may be applied to all of the transfer electrodes except for one transfer electrode to make the charge be converged in the potential well below the one transfer electrode and the signal charge can be transferred in the transferring direction.

In the first embodiment, only the transfer electrode 2212 is larger than the other transfer electrodes. However, the plurality of transfer electrodes can be arranged so that their sizes gradually become small starting from the IG electrode 2211 toward the OG electrode 2219. Similarly, in the second embodiment, the number of sequential transfer electrodes to which ON voltage is applied at the same time can be decreased gradually to move the signal electrode toward the OG electrode 2219.

Further, in the first to third embodiments, the description is given by taking the CCDs as an example for the charge transfer method. However, the charge transfer method is not limited to the above example. For example, charge transferring can be performed by using BBDs (Bucket Bridged Devices).

In the second embodiment, the size of the charge accumulation regions in the phasing adder 220b is controlled by the drive controller 24. However, a control signal relating to the setting may be input from outside the ultrasound probe 2, that is, from the main body 1, and only the operation based on the setting may be performed in the phasing adder 220b.

Furthermore, although the ultrasound probes 2 which can transmit and receive ultrasound waves are described in the first to third embodiments, the ultrasound probes 2 may be ultrasound probes used exclusively for reception of ultrasound waves.

In the first to third embodiments, sending and receiving of control signals and received data on ultrasound waves are performed though wireless communication. However, the sending and receiving may be performed through wired communication using a cable. Moreover, the present invention can also be applied to the part relating to reception of ultrasound waves in a probe integrated ultrasound diagnosis apparatus which detects ultrasound waves.

Fourth Embodiment

Next, the ultrasound probe of the fourth embodiment which utilizes the acoustic sensor of the present invention will be described.

Figure 10:
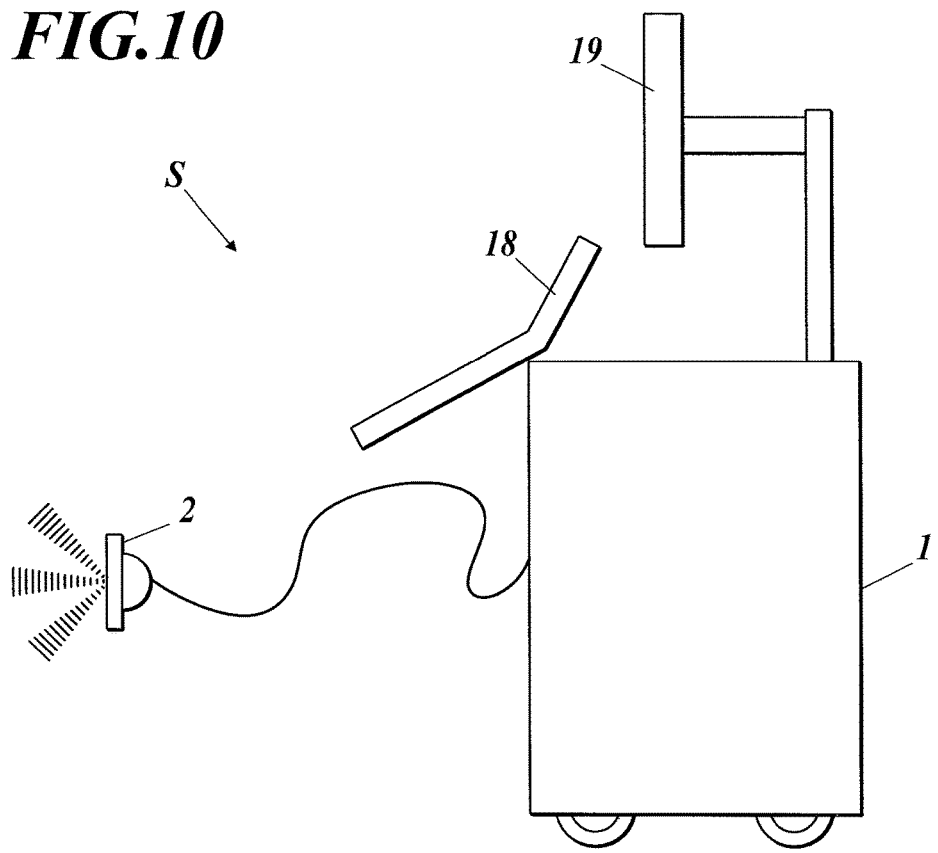
FIG. 10 is an overall view showing an ultrasound diagnosis apparatus of the fourth embodiment.
Figure 11:
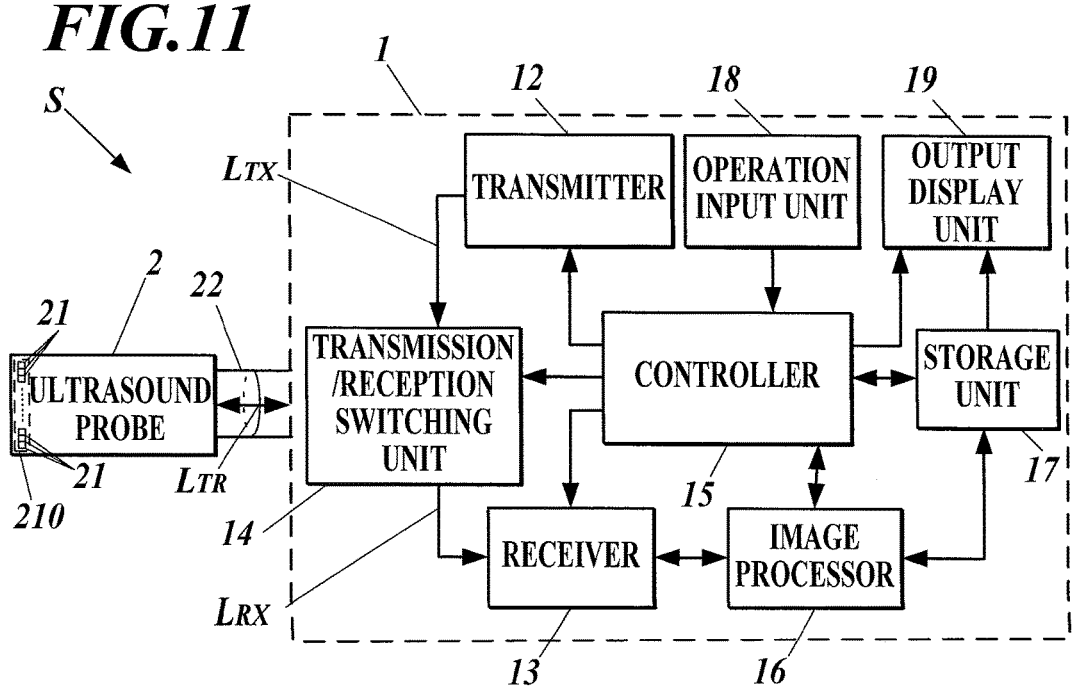
FIG. 11 is a block diagram showing an inner structure of the ultrasound diagnosis apparatus.

FIG. 10 is an overall view of the ultrasound diagnosis apparatus Sa of the embodiment provided with an ultrasound probe utilizing the acoustic sensor. FIG. 11 is a block diagram showing the inner structure of the ultrasound diagnosis apparatus Sa.

As shown in FIG. 10, the ultrasound diagnosis apparatus Sa includes a main body 1 and an ultrasound probe 2a which is connected to the main body 1 via a cable 29. The main body 1 is provided with an operation input unit 18 and an output display unit 19. The controller 15 of the main body 1 outputs drive signals to the ultrasound probe 2a to make the ultrasound probe 2a output ultrasound waves, obtains received signals relating to reception of ultrasound waves from the ultrasound probe 2a to perform various processes and displays results and the like in a liquid crystal screen of the output display unit 19 as needed on the basis of input operations from outside performed on input devices such as a key board and a mouse in the operation input unit 18.

As shown in FIG. 11, the main body 1 includes a transmitter 12, a receiver 13, a transmission/reception switching unit 14, a controller 15, an image processor 16 (signal processor), a storage unit 17, an operation input unit 18, an output display unit 19 (output unit), etc.

According to a control signal sent from the controller 15, the transmitter 12 supplies pulse signals to the ultrasound probe 2a to cause the ultrasound probe 2a to generate ultrasound waves. The transmitter 12 includes, for example, a clock circuit, a pulse circuit, a pulse width determiner, and a delay circuit. The clock circuit generates clock signals which determine the timing and the frequency of transmitted pulse signals. The pulse circuit generates bipolar rectangular pulses with a predetermined voltage or amplitude in a given cycle. The pulse width determiner sets the width of rectangular pulses transmitted from the pulse circuit. Rectangular pulses generated at the pulse circuit are separated into different wiring paths for respective transducers 210 in the ultrasound probe 2 either before or after the rectangular pulses enter the pulse width determiner. In response to a timing with which generated rectangular pulses are transmitted to the transducers 21, the delay circuit delays the transmission of the pulses by individual delay times set for the respective wiring paths.

The receiver 13 is a circuit for acquiring signals sent from the ultrasound probe 2a under the control of the controller 15. The receiver 13 includes, for example, an amplifier, an analog-to-digital (A/D) converter, and a phasing addition circuit. The amplifier is a circuit for amplifying individual signals in response to respective ultrasound waves received at the respective transducers 210 in the ultrasound probe 2a by a predetermined amplification factor. The A/D converter converts the amplified signals into digital data at a predetermined sampling frequency. The phasing addition circuit phases the A/D converted signals by giving individual delay times to the respective wiring paths for the respective transducers 210, and adds up the phased signals to create sound ray data.

The transmission/reception switching unit 14 switches transmission and reception operations under the control of the controller 15: The transmitter 12 sends driving signals to the transducers 210 so that the transducers 210 emit ultrasound waves; while the receiver 13 transmits receiving signals to the transducers 210 so that the receiver 13 acquire signals in response to ultrasound waves received at the transducers 210, through operation of the transmission/reception switching unit 14.

The controller 15 includes a central processing unit (CPU), a hard disk drive (HDD), and a random access memory (RAM). The CPU reads programs stored in the HDD and loads them onto the RAM. Under instruction of the loaded programs, the CPU comprehensively controls the operation of each component in the ultrasound diagnostic apparatus Sa. The HDD stores control programs and processing programs for operating the ultrasound diagnostic apparatus Sa, and various setting data and other information. These programs and setting data may be stored, for example, in any readable and rewritable auxiliary storages composed of nonvolatile memory such as flash memory, other than the HDD. The RAM is static random access memory (SRAM), dynamic random access memory (DRAM), or any other volatile memory. The RAM provides working area for the CPU and stores temporary data.

The image processor 16 includes a processor module, which is separate from the CPU of the controller 15. The image processor 16 performs arithmetic operations to generate diagnostic images based on data received through ultrasound waves. The diagnostic images include image data and video data composed of a series of still images, which are displayed on the output display 19 in roughly real time, and still images of snapshots. The arithmetic operations may be performed by the CPU of the controller 15.

The storage unit 17 is, for example, DRAM or any other volatile memory. Alternatively, the storage unit 17 may be any kind of nonvolatile memory which allows rewriting data at high speeds. The storage unit 17 stores diagnostic image data for real-time display, which is processed at the image processor 16, in units of frames. Under the control of the controller 15, image data for ultrasound diagnosis stored in the storage unit 17 is read, and is sent to the output display unit 19 or output to the exterior of the ultrasound diagnostic apparatus Sa via a communication unit (not shown). If the output display unit 19 is based on a television system to display data, a digital signal converter (DSC) should be provided between the storage unit 17 and the output display unit 19 so that the scanning format of image data is converted and then the image data is sent to the output display unit 19.

The operation input unit 18 includes a push button switch, a keyboard, and either a mouse or a trackball, or a combination thereof. The operation input unit 18 converts an input operation by the user to an operation signal and inputs the operation signal into the main unit 1.

The display unit 19 includes a screen and a drive unit therefor. The display is any one of a liquid crystal display (LCD), an organic electroluminescent (OEL) display, an inorganic electroluminescent display, a plasma display, a cathode ray tube (CRT) display, and any other display. In accordance with control signals output from the CPU of the controller 15 and image data generated by the image processor 16, the output display unit 19 produces signals for driving the display screen (picture elements) to display a menu and a status indication depending on the ultrasound diagnosis and measurements obtained through received ultrasound waves on the screen.

The operation input unit 18 and the output display unit 19 may be integrated with the main unit 1, or may be disposed externally and connected to the main unit 1 via USB cables or any other connector. Alternatively, if the main unit 1 includes terminals for operational input and display output, the operation input unit 18 and the display 19 can be conventional peripheral devices that are connected to these terminals.

The ultrasound probe 2a acts as an acoustic sensor which generates and emits ultrasound waves (about 1 to 30 MHz in this embodiment) toward a subject such as a living body, receives echoes of the emitted ultrasound waves, which are reflected off the subject, and converts the echoes into electric signals. The ultrasound probe 2a includes a transducer array 210, i.e. a transducer array 21 for transmitting and receiving ultrasound waves, and a cable 29. The cable 29 has a connector (not shown) for the main unit 1, at its one end. The ultrasound probe 2a is detachably connected to the main unit 1 via the cable 29.

The transducer array 21 is an array of transducers 210. Each transducer 210 includes a piezoelectric element and electrodes on two sides. An electric charge appears on these electrodes when the piezoelectric element is deformed (expansion and contraction). The transducer array 21 is, for example, a one-dimensional array. Voltage pulses (pulse signals) supplied to the transducers 210 generate an electric field in each of the piezoelectric elements. The electric field deforms the piezoelectric element, which generates and emits ultrasound waves. The sound pressure of ultrasound waves of predetermined frequencies incident on each of the transducers 210 causes a vibration or oscillation in each piezoelectric element in the thickness direction. As a result, an electric charge with an amount in response to the oscillation appears at each end in the thickness direction of the piezoelectric element. This induces an electric charge with an amount in response to that of the electric charge on the electrode of the piezoelectric element. In this embodiment, the piezoelectric elements are composed of a ferroelectric material. The intensity of the electric field generated in the ferroelectric material during transmission and reception of ultrasound waves is smaller than that of the coercive electric field of the ferroelectric material.

Figure 12:
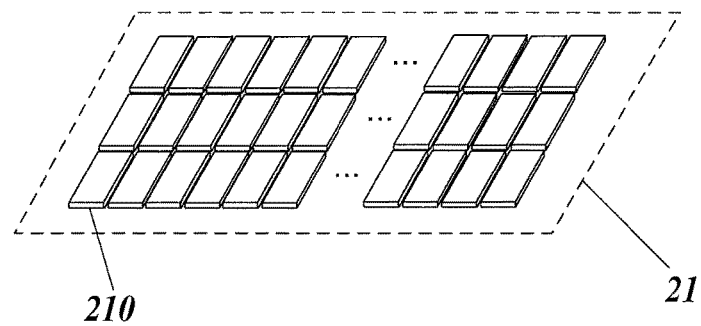
FIG. 12 is a diagram used to explain an example of a transducer array.

FIG. 12 is a diagram used to explain an example of the transducer array 21 in the ultrasound probe 2a.

In the ultrasound probe 2a of the embodiment, for example, 576 transducers 210 (3 (width direction)×192 (scanning direction) are arranged in a two dimensional array in the transducer array 21. Alternatively, the transducers 210 may be arranged in one dimensional array in the scanning direction. Further, the number of transducers 210 can be set arbitrarily. The ultrasound probe 2a may adopt electrical scanning or mechanical scanning. The scanning may be any of linear scanning, sector scanning, and convex scanning. Any frequency range in which the ultrasound probe 2a receives ultrasound waves can be set.

The ultrasound diagnostic apparatus Sa may be configured to allow any one of the multiple ultrasound probes 2a to be connected to the main unit 1 depending on the subject undergoing diagnosis.

Figure 13:
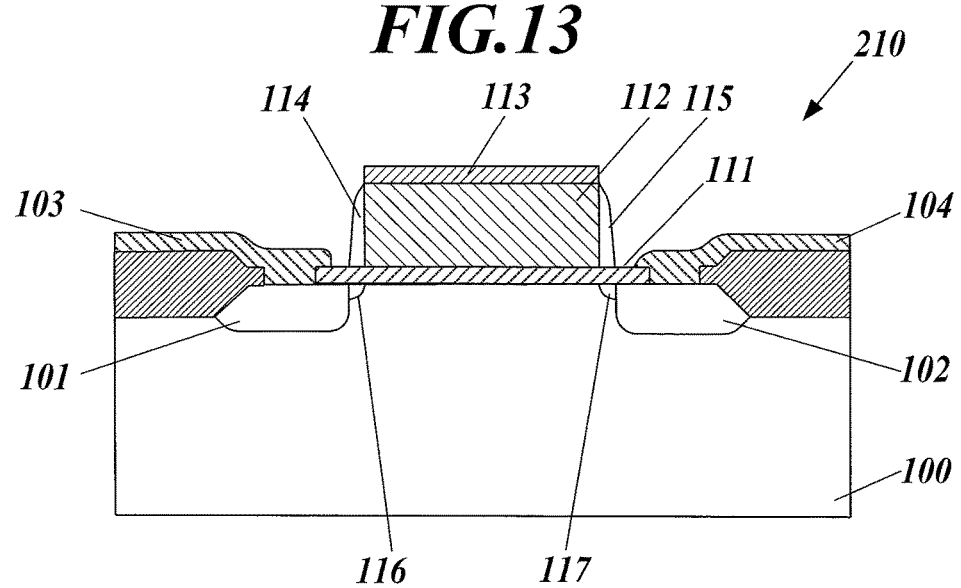
FIG. 13 is a schematic view showing a cross-sectional structure of a transducer.

FIG. 13 shows a cross-sectional structure of one transducer 210 relating to sending and receiving of an ultrasound wave.

Each transducer 210 of the embodiment is formed as a semiconductor chip including a semiconductor substrate 100, a ferroelectric thin film 112 (piezoelectric thin film) laminated on the semiconductor substrate 100 with a gate insulation film 111 therebetween and a gate electrode 113 laminated on the ferroelectric thin film 112. Two sides of the ferroelectric thin film 112 are provided with side walls 114 and 115, respectively. On the upper surface of the semiconductor substrate 100, extension regions 116 and 117 (conductive regions), a source region 101 and a drain region 102 are formed with the region below the gate electrode 113 (a predetermined region, the part which is the channel region) between them and the semiconductor substrate 100. The source region 101 and the drain region 102 are connected to metal leads 103 and 104, respectively.

The semiconductor substrate 100 is a p-type silicon substrate. Negative ions of chemical elements, such as phosphorus and arsenic, are injected into the semiconductor substrate 100 to form an extension regions 116 and 117, and the source region 101 and the drain region 102 are further formed.

The source region 101 is grounded via the metal lead 103. The drain region 102 is connected to the signal output via the metal lead 104. The gate electrode 113 can be connected with the voltage supply unit via the voltage apply circuit (not shown) provided on the semiconductor substrate 100, and the bias voltage that flow across the gate and source is applied to the gate electrode 113. Polarization of the ferroelectric thin film 112 is changed according to the bias voltage due the bias voltage being applied to the ferroelectric thin film 112. On the other hand, the gate electrode 113 is normally kept to be in a floating state or in a grounded state. Due to the ultrasound waves being incident on the ferroelectric thin film 112, charges according to the ultrasound wave intensity (sound pressure) and the polarization occur at both ends (both sides) of the ferroelectric thin film 112. The conductive state of the channel region between the source region 101 and the drain region 102 changes according to the charge generated on the side of the ferroelectric thin film 112 that faces the gate insulation film ill and the charge that flow across the source and drain is output to the semiconductor substrate 100 from the drain region 102 as a signal.

The ferroelectric material is, for example, lead zirconate titanate (PZT) in the form of a thin film (typically less than 10 µm, preferably less than 1 µm). The surface area and the thickness of the ferroelectric thin film 112 are determined depending on the reception frequencies of ultrasonic waves are, while the length of the channel between the source region 101 and the drain region 102 is appropriately maintained. Examples of such ferroelectric materials include ferroelectric materials with a perovskite structure, a tungsten bronze structure, and a bismuth layered structure, organic ferroelectric materials, such as polyvinylidene fluoride (PVDF) and PVDF copolymers, and composites of these materials. These ferroelectric materials are of a multi-domain structure and/or of a polycrystalline structure under normal conditions.

A ferroelectric thin film 112 and a gate electrode 113 are deposited on the semiconductor substrate 100 by a sputtering (physical vapor deposition (PVD)) process, a sol-gel process, a chemical-vapor deposition (CVD) process, or any other process. The ferroelectric thin film 112 and the gate electrode 113 are then formed by, for example, photo etching of the thin films through a photoresist layer or any other photomask tailored to the structures of the ferroelectric thin film 112 and the gate electrode 113. After an insulating film of, for example, silicon dioxide ($SiO_2$) is deposited on the semiconductor substrate 100, the ferroelectric thin film 112, and the gate electrode 113 by a chemical-vapor deposition (CVD) process or any other process, the insulating film is etched into side walls 114 and 115. The source region 101 and the drain region 102 are formed by self-alignment by ion injection through the gate electrode 113 and the side walls 114 and 115 functioning as photomasks. The metal leads 103 and 104 are then provided so as to be connected to the gate electrode 113, the source region 101, and the drain region 102.

The plurality of transducers 210 and the ferroelectric thin films 112 (blocks) corresponding to individual transducers 210 may be formed individually. However, by forming a plurality of them at once on one or only few pieces of wafers, the transducer array 21 can be formed easily and at low cost while accurately arranging the plurality of transducers 210.

Since each transducer 210 in the ultrasound probe 2 includes a ferroelectric thin film 112, the ferroelectric layer is distributed evenly. Thus, the ferroelectric thin films 112 exhibit polarizations with reliable accuracy in response to the intensities of incident ultrasound waves. Also, such a thin film can be activated at a sufficiently low voltage for causing the coercive electric field necessary for polarity reversal. As a result, even after the circuit of the transducer 21 is formed, a voltage can be easily applied to the ferroelectric thin films 112 to change the polarity. In this case, the thickness of the ferroelectric thin films 112 should be determined so that the withstand voltages at portions, for example, the dielectric breakdown voltage of the gate insulating film 111, withstand voltage between the drain and the source, withstand voltage between the p- and n-wells, and withstand voltage between the wells and the semiconductor substrate 100, are larger than the maximum voltage applied to the ferroelectric thin film 112 to generate an coercive electric field. Under normal conditions, the withstand voltages at these portions range from ten to several tens of volts. Thus, the voltage for causing the coercive electric field should be smaller than these values. The coercive electric field is approximately 1 MV/m although it depends on the ferroelectric material, the proportion of the components, the crystal system, and other factors. In order to achieve a voltage for causing the coercive electric field of less than the withstand voltage, the thickness of the ferroelectric thin film 112 should be 1 µm or less in view of the influence of the thickness of the gate insulating film.

Further, if transmission of ultrasound waves are to be performed by using the ferroelectric thin films 112, the voltage applied at the time of transmission can also be small according to the film thickness. The voltage can be set to an appropriate value within the range the heat generation causes no problem without changing the polarization in the range smaller than the coercive electric field voltage.

The transducer 210 according to this embodiment can receive ultrasound waves not only when each region is polarized in a uniform direction but also when the polarizing direction in each region is not uniform in varying degrees. When ultrasound waves enter the ferroelectric thin film 112 with a uniform polarization direction, the entire ferroelectric thin film 112 is deformed in response to the sound pressure of the ultrasound waves, like an ordinary piezoelectric element. As a result, electric charges appear at each side in response to the deformation. When ultrasound waves enter the ferroelectric thin film 112 of multi-domain structure and/or of a polycrystalline structure with the polarizing direction in each region varying, no expansion or contraction occur in the ferroelectric thin film 112 as a whole. In other words, no charge appears at each end because of no overall deformation. With respect to the polarization direction having a uniformity degree in the middle of the above two degrees, the charge amount generated is also an intermediate amount.

The polarization of the ferroelectric thin film 112, however, does not vary in proportion to the strength of the electric field appearing in the ferroelectric thin film 112. This problem can be resolved by referring a table of the correspondence between target polarizations and electric fields (applied voltages) essential for the target polarizations preliminarily stored on the HDD of the controller 15 or any other storage. The current polarization of the ferroelectric thin film 112 is changed to a desired level with reference to this table to obtain an applied voltage required for the desired polarization, and supplying the applied voltage from the voltage supply unit to the gate electrode 113. Alternatively, a table listing only the correspondence between a specified polarization and target polarizations may be stored so that the current polarization is changed to a desired polarization by way of the specified polarization.

In the ultrasound probe 2a of the embodiment, the polarization of each transducer 210 in the transducer array 21 can be set individually. That is, with respect to the lead between the voltage supply unit and each gate electrode 113, at least a part thereof that connects with each gate electrode 113 is provided individually. In response to the control signals from the controller 15, voltages can be supplied only to the desired transducers 210 via switching elements which can switch between on and off. Alternatively, voltage dividers may be provided respectively in the middle of individual leads, and a predetermined voltage output from the voltage supply unit may be divided into desired voltages to be applied to the ferroelectric thin films 112 of individual transducers 210. In such case, if the ultrasound probe 2a is provided with a resistance element as a load for partial voltages, the size of a transducer 210 may be larger comparing to a semiconductor chip. Therefore, an appropriate voltage may be generated by combining a plurality of small volume capacitors. Alternatively, partial voltages may be generates in the main body 1 to be supplied respectively to the ferroelectric thin films 112 of the ultrasound probe 2a.

Various patterns can be suggested as polarization setting patterns of the transducers 210. For example, by changing the polarization of each transducer 210 according to its position, weighting of receiving sensitivity can be set for each transducer 210. That is, conventional weighting has been set for each transducer 210 by individually changing the amplification factor of the amplifier and a process relating to spatial correlation such as forming of a receiving window (specifically, apodization) can be performed without adjusting polarization factor.

Further, the receiving sensitivity of the transducers 210 at the positions where ultrasound reception is not desired may be dropped to a zero level in order to reduce the influence of artifacts and the like to change the polarization so as to form receiving windows (for example, Hanning windows).

Figure 14:
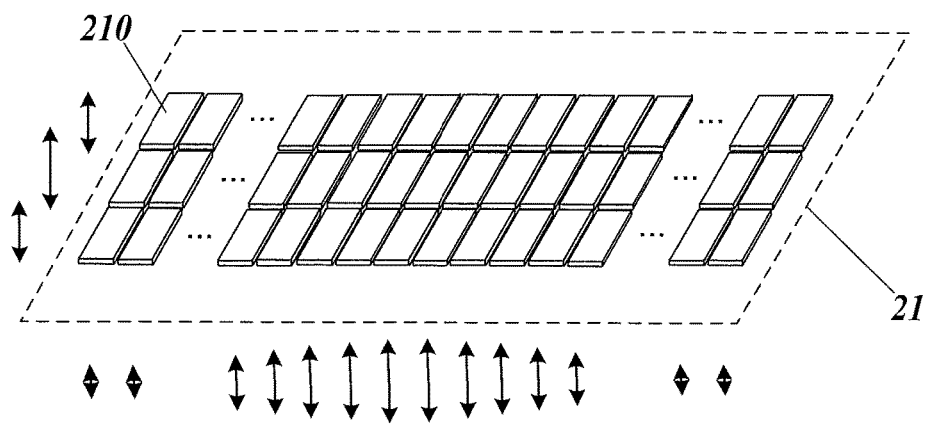
FIG. 14 is a schematic view showing a polarization setting in the transducer array.

FIG. 14 is a schematic view showing the polarization setting of the transducers 210 in the transducer array 21 arranged in a two dimensional manner.

Here, the tendency of polarization levels are indicated by double-headed arrows. In the transducer array 21, the polarization levels of the ferroelectric thin films 112 of the transducers 210 at the middle part are large. That is, it is set that the regions (grain) of the multi-domain structure and of the polycrystalline structure are polarized in a uniform direction. Further, in the transducer array 21, the polarization levels of the ferroelectric thin films 112 are set so as to decrease gradually as approaching toward the transducers 210 at the four corners. That is, it is set that the multi-domain structure and the polycrystalline structure are not polarized in a uniform direction. Thereby, the apodization setting is set so that the receiving sensitivity of the transducers 210 at the center part be high and the receiving sensitivity of the transducers 210 at the four corners be low.

Here, the polarization level (receiving sensitivity) gradually decreases as approving the ends from the center in all two dimensional directions. However, the polarization degree may be changed only in the scanning direction.

As described above, the acoustic sensor used in the ultrasound probe 2a of the fourth embodiment includes the transducers 210 each of which has a ferroelectric thin film 112 (piezoelectric thin film) directly or indirectly laminated on the semiconductor substrate 100. In each transducer 210, the conductive state of the channel region in the semiconductor substrate 100, that is, the amount of charge that flows varies on the basis of the charge amount induced in the ferroelectric thin film 112 in response to the sound pressure incident on the ferroelectric thin films 112. Each transducer 210 outputs a signal according to the conductive state.

In a conventional acoustic sensor, a transducer including a piezoelectric element is formed as a laminated board by a thick coating technique in a plate manner or a thick film manner (usually, 10 μm or thicker, generally 100 μm or thicker), for example. Such conventional acoustic sensor measures the ultrasound wave strength by detecting the deformation of the transducers in their thickness direction due to the ultrasound waves incident on the board surfaces. However, with ultrasound diagnosis apparatuses becoming to have high resolution and high sensitivity, high accuracy is desired in ultrasound probes. In order to make the piezoelectric members of the acoustic sensors used for reception of ultrasound waves in a conventional ultrasound probe have high accuracy, the manufacturing processes are complicated and increase in size was unavoidable. In response to the above, by receiving ultrasound waves with thin film formed by a spattering method as described above, a highly accurate piezoelectric layer can be formed easily. Therefore, data having high resolution and high dissolution can be obtained easily.

Further, by changing the conductive level of a channel region in the semiconductor substrate 100 by the electric field generated by the charge induced in the ferroelectric thin film 112 in response to the ultrasound wave incident thereon, the conductive state of the channel region is changed. Therefore, such acoustic sensor can be manufactured easily at low cost by the conventional FeRAM manufacturing process.

Furthermore, a plurality of transducers 210 respectively including ferroelectric thin films 112 are arranged in a two dimensional manner or one dimensional manner, and each transducer outputs a signal relating to the receiving intensity of an ultrasound wave. Thus, the transducer array 21 can be formed in a compact manner.

Moreover, the transducers 210 can be formed together on one or a few pieces of wafers. Therefore, the transducer array 21 can be formed easily at a low cost while arranging the plurality of transducers 210 accurately.

With respect to the ferroelectric thin films 112, they are formed of a ferroelectric material such as PZT and they are formed so as to be smaller than the withstand voltage of the transducers 210 in which coercive electric field voltage is generated, the coercive electric field voltage reverses the polarization of the ferroelectric thin films 112. Therefore, the ferroelectric thin films 112 can be adjusted to appropriate polarization and the transducers 210 can receive ultrasound waves with appropriate sensitivity. Further, since such setting of polarization can be performed after the transducers 210 and the transducer array 21 are formed, lowering of sensitivity over time can be easily taken care of.

Each transducer 210 is provided with a voltage applying circuit for setting the polarity of its corresponding ferroelectric thin film 112. Therefore, polarization of each ferroelectric thin film 112 can be adjusted easily with internal controlling in the ultrasound probe 2a and the ultrasound diagnosis apparatus 1.

Since the voltage applying circuit is provided in each transducer 210 so as to individually set the polarization, the sensitivity can be adjusted easily in each transducer 210. Further, weighting of spatial sensitivity and forming of receiving windows can be carried out according to the receiving condition. Therefore, artifact reduction and the processes which conventionally have been performed by adjusting the amplification factor of the amplifier can be carried out in the transducers 210.

The controller 15 which decides the polarization of the ferroelectric thin films 112 and which controls the operation of the voltage applying circuits according to the decided polarization is included. Therefore, detail settings such as weighting of sensitivity in each transducer 210 can be performed easily, frequently and quickly.

The controller 15 can decide the polarization according to the process relating to spatial correlation such as apodization that is performed on the received sound waves. Therefore, processes such as switching between output and do-not-output of received signals by the switching elements and adjustment of amplification factor of the amplifier can be simplified or omitted.

By adapting the above described acoustic sensor in the ultrasound probe 2a, the ultrasound probe 2a can have high resolution and high dissolution and can be formed in a compact manner with light weight.

By using the ultrasound diagnosis apparatus Sa including the image processor 16 which analyzes the signals relating to the ultrasound waves received by the ultrasound probe 2a and the output display unit 19 which outputs the analysis results of the image processor 16 in a predetermined format, a user can perform an ultrasound diagnosis based on a highly accurate and highly sensitive ultrasound image easily and at a low cost.

Fifth Embodiment

Next, the ultrasound probe 2a of the fifth embodiment will be described.

The ultrasound probe 2a has the configuration similar to that of the ultrasound probe 2a of the fourth embodiment except that the configuration of the transducers 210b being different from that of the transducers 210 of the fourth embodiment. The same reference numerals are used for the same parts and their description is omitted.

Figure 15:
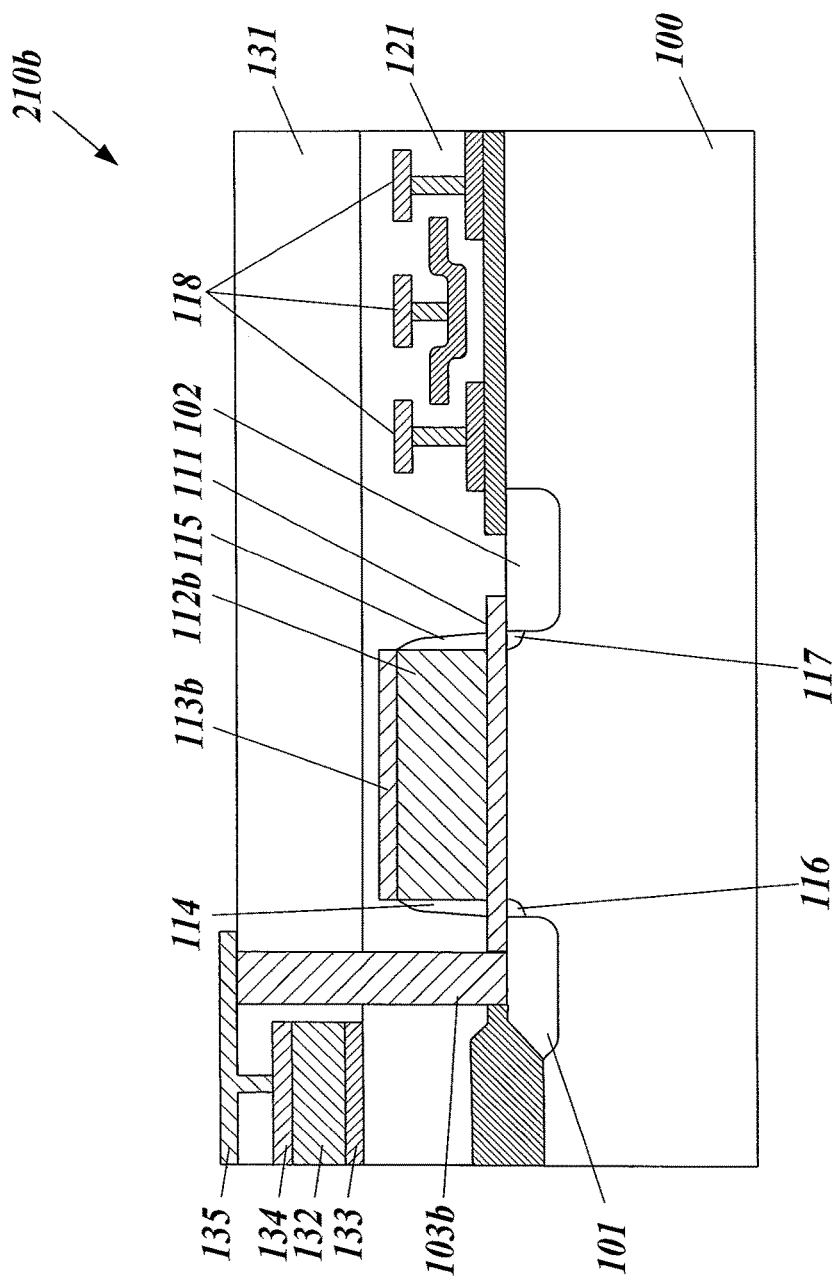
FIG. 15 is a schematic view showing a cross-sectional structure of a transducer of the fifth embodiment.

FIG. 15 is a diagram used to explain the cross-sectional structure of one transducer 210b relating to sending and receiving of an ultrasound wave in the ultrasound probe 2a of the fifth embodiment.

Each transducer 210b in the ultrasound probe 2a of the embodiment is provided with a p-type semiconductor substrate 100, a gate electrode 112b (electrode) and a metal lead 113b which are laminated on the p-type semiconductor substrate 100 via the gate insulating film 111. Further, this gate electrode configuration is buried in the insulating films 121 and 131. The source region 101 is connected with a contact plug 103b which penetrates the insulating films 121 and 131.

Here, the drain region 102 is near the transfer electrodes 118 which are arranged in a line.

On the insulating film 121, the electrode 133, the ferroelectric thin film 132 and the electrode 134 are laminated in this sequence to form a ferroelectric capacitor as a piezoelectric device. Either one of the electrodes 133 and 134 (here, the electrode 134) is connected with the contact plug 103b via the metal lead 135.

The transfer electrodes 118 are formed of a metal material, and ON voltage is sequentially applied to them to form a potential well in the semiconductor substrate 100 below the transfer electrodes 118. By the position of this potential well moving overlapping the transfer electrodes 118, the charge flowed in to the drain region 102 is transferred across the semiconductor substrate 100 with the formed potential well according to the principal of CCD (Charge Coupled Device).

The gate electrode 112b is formed of polysilicon, for example. By a predetermined voltage being supplied to the gate electrode 112b from the voltage supply unit which is connected via the metal lead 113b, the voltage is applied across the gate and the source to change the conductive state of the channel region between the source region 101 and the drain region 102 in the semiconductor substrate 100 below the gate electrode 112b.

As for the insulating films 121 and 131, silicon insulating films using silicon dioxide are used. After the insulating films 121 and 131 are formed, a mask is formed by a photoresist, a contact hole is formed by etching and tungsten or the like is injected in the contact hole. Thereafter, the contact plug 103b is formed by grinding by etching back or CMP (chemical mechanical polishing).

The electrode 134 of the ferroelectric capacitor is maintained grounded. On the other hand, the electrode 133 is connected to the source region 101, and charges are generated at both ends of the ferroelectric thin film 132 when an ultrasound wave is incident on the ferroelectric thin film 132 causing a current flow between the electrode 133 and the source region 101. By applying a predetermined voltage to the metal lead 113b and the gate electrode 112b so that the channel region is in the conductive state at the time of ultrasound wave reception, the current is further sent to the signal output from the drain region 102 via the channel region.

The electrode 133 can be further connected with the voltage supply unit, and an electric field can be generated between the electrodes 133 and 134 by a predetermined voltage being supplied to the electrode 133 from the voltage supply unit to change the polarization of the ferroelectric thin film 132.

As for the ferroelectric thin films 132, the ferroelectric elements which are the same as that of the ferroelectric thin films 112 of the transducers 210 of the ultrasound probe 2a of the fourth embodiment may be used. The ferroelectric thin film 132 of each ferroelectric capacitor has an area according to the receiving frequency of the ultrasound wave. At this time, although each ferroelectric thin film 132 is not limited in relation to the channel length, the ferroelectric thin films 132 are to have a shape and are to be arranged according to the spatial resolution and the like of the ultrasound probe 2a relating to a plurality of transducers 210b. Although the ferroelectric capacitor and the FET are shown in about same sizes in FIG. 15, this is due to schematic purposes. In reality, the FET can be made smaller but the size of the ferroelectric capacitor cannot be made smaller with respect to the receiving frequency of the ultrasound wave. Therefore, the ferroelectric capacitor has a larger size comparing to the FET.

As described above, each transducer 210b in the ultrasound probe 2a of the fifth embodiment is provided with the gate electrodes 112b for switching the conductivity of the channel regions, the gate electrodes 112b being provided on the semiconductor substrates 100. With respect to each transducer 210b of the ultrasound probe 2a of the fifth embodiment, the ferroelectric thin film 132 is disposed so as to be connected with one end of the channel region via the electrode 134, the metal lead 135 and the contact plug 103b so that the charge amount (conductive state) that flows across the channel region changes due to the charge according to the charge amount that is induced in the ferroelectric thin film 132 in response to an ultrasound wave being incident thereon flows across the channel region when the channel region is conductive by a predetermined voltage being applied to the gate electrode 112b.

By leading the charge in to the channel region by having the ferroelectric capacitor as described above, the FET configuration relating to signal output can be downsized easily while matching the size of the ferroelectric capacitor (the ferroelectric thin film 132) relating to ultrasound wave reception to the size of the received frequency. Further, since the ferroelectric element is formed of a thin film, an acoustic sensor having high accuracy can be provided in a stacking configuration with the FET configuration in a compact manner.

The present invention is not limited to the fourth and fifth embodiments, and can be modified in various ways.

For example, although the ferroelectric thin films are used in the fourth and fifth embodiments, an acoustic sensor using regular piezoelectric thin films that do not have ferroelectric characteristics or such characteristics are weak may similarly apply the present invention thereto. In such case, since a predetermined polarization cannot be maintained, the configuration for performing polarization setting by applying a voltage across the gate and the source from the voltage supply unit. On the other hand, in a case where apodization is to be performed, the amplification level of the amplifier needs to be changed as in the conventional case.

Even in a case where the ferroelectric thin films are used, polarization adjustment is to be performed only when dealing with deterioration over long period of time. Usually, change in amplification level of an amplifier and apodization by switching of switching elements and window setting may be performed.

In the fourth embodiments, the gate oxide film is disposed between the ferroelectric thin film and the silicon substrate. However, similarly to the MOSFET configuration, the ferroelectric thin film may be directly laminated on the silicon substrate without having the gate oxide film therebetween.

In the fifth embodiment, the conductivity state is controlled via the FET type transistor. However, the conductivity state may be controlled via a bipolar type transistor. In such case, the ferroelectric thin film is connected to an emitter instead of the source region. Further, as for the withhold voltage to be compared to the coercive electric field voltage, a withhold voltage between regions such as a base, an emitter and a collector are included.

In the fifth embodiment, the embodiment where the charge relating to one ferroelectric capacitor is passed to the channel region of one FET is taken as an example. However, the configuration may be such that two sets of such embodiment are used complementary. In such case, two ferroelectric capacitors whose polarization is uniform in the same direction are used, and charge signals can be output from the n-channel FET and the p-channel FET. Alternatively, in a case where the polarization of the two ferroelectric capacitors are opposite to each other, charge signals corresponding to the amplitude intensity of the ultrasound wave in a rectified form from the n-channel FET and the p-channel FET.

In the fourth and fifth embodiments, their description is given by taking the ultrasound probe relating to the medical ultrasound diagnosis apparatus as an example. However, the ultrasound probe may be applied to an ultrasound diagnosis apparatus used for internal inspection of an architectural building. In such case, the acoustic sensor part which sends and receives ultrasound waves does not need to be provided outside the main body as an ultrasound probe. The acoustic sensor part may be provided integrally with the main body.

The transducers of the present invention as the acoustic sensors do not need to be used in an ultrasound diagnosis apparatus. Instead, the transducers may be merely used in a measuring apparatus which measures the receiving intensity of ultrasound waves. In such case, only one acoustic sensor may be used and a plurality of acoustic sensors are not needed.

In the fourth and fifth embodiments, a case where ultrasound waves of 1 to 30 MHz are received is described. However, the present invention may be applied to an acoustic sensor which receives a sound wave of a frequency band that can be received if the piezoelectric member is formed in a thin film manufacturing process.

In the fourth and fifth embodiment, the configuration where the controller is provided only in the main body 1 to send control signals to the ultrasound probe 2a is described. However, some of the controlling may be performed in the ultrasound probe 2a according to the power consumption, size, weight and the like. In such way, the amount of control signals that goes through the cable 29 can be reduced. Alternatively, the setup data may be held in the ultrasound probe 2a and for example, polarization setting and the like may be carried out in the ultrasound probe 2a by utilizing the setup data on the basis of the control signals from the main body 1.

Specific details of the configuration and structure described in the above embodiments may be arbitrarily modified within the scope of the invention.

The entire disclosure of Japanese Patent Application No. 2014-049692 and Japanese Patent Application No. 2014-049731 filed on Mar. 13, 2014 including description, claims, drawings, and abstract are incorporated herein by reference in its entirety.

What is claimed is:

1. A phasing adder for processing charges generated in a plurality of piezoelectric devices respectively having piezoelectric elements which generate the charges in response to sound pressure of input ultrasound waves, the phasing adder comprising:

(i) a plurality of delay charge transfer units,
   wherein:
   each delay charge transfer unit includes a plurality of stages including a first stage which comprises a first holding unit, and subsequent stages which each comprise a holding unit;
   each delay charge transfer unit obtains signal charge amounts that are not amplified, the signal charge amounts being obtained according to the charges generated in a corresponding one of the plurality of piezoelectric devices, and performs sending and receiving of the signal charge amounts across a predetermined number of the plurality of stages while holding the signal charge amounts for a predetermined time in each of said predetermined number of the plurality of stages;
   each delay charge transfer unit obtains and holds the signal charge amounts in the first holding unit of the first stage at a time of ultrasound wave reception, and, thereafter, holds the signal charge in the holding units of subsequent stages which follow the first stage, from among the predetermined number of the plurality of stages; and
   in each delay charge transfer unit, electric capacitance of the first holding unit of the first stage is greater than electric capacitance of each of the holding units of the subsequent stages; and (ii) a delay adder which performs phasing addition of the signal charge amounts which are held and transferred across the predetermined number of the plurality of stages in each delay charge transfer unit.

2. The phasing adder of claim 1, wherein, in each delay charge transfer unit, the electric capacitances of the holding units of the subsequent stages are equal to each other.

3. The phasing adder of claim 1, wherein the electric capacitance of each first holding unit is variable.

4. The phasing adder of claim 3, wherein:
charge holding units in a number more than a number of the plurality of stages are formed in each delay charge transfer unit, and
the electric capacitance of each first holding unit is varied by adjusting the plurality of charge holding units to be used integrally to hold the signal charges.

5. The phasing adder of claim 4, wherein electric capacitances of the charge holding units are equal to each other.

6. The phasing adder of claim 3, wherein the electric capacitance of each first holding unit is set independently according to a corresponding piezoelectric device.

7. The phasing adder of claim 1, wherein:
each delay charge transfer unit is formed as a semiconductor chip, and
each first holding unit is connected to a corresponding piezoelectric element or is disposed near the corresponding piezoelectric element.

8. The phasing adder of claim 7, wherein CCDs are used for the delay charge transfer units.

9. An ultrasound probe, comprising:
the phasing adder of claim 1;
a plurality of piezoelectric devices which receive ultrasound waves, which generate charges in response to sound pressure of the received ultrasound waves, and which send the charges to the phasing adder to be held in the first holding units of the respective corresponding delay charge transfer units;
a signal amplifier which receives the charges which are subjected to phasing addition and output by the phasing adder, and which amplifies the received charges output by the phasing adder as a voltage signal; and
a signal output unit which outputs the amplified voltage signal.

10. The ultrasound probe of claim 9, wherein:
electric capacitances of the first holding units are variable, and
the first holding units include a controller for setting the electric capacitances of the first holding units.

11. The ultrasound probe of claim 10,
wherein at the time of ultrasound wave reception by the plurality of piezoelectric devices, the controller individually changes the electric capacitances of the first holding units respectively corresponding to the piezoelectric devices according to receiving directions of ultrasound waves and time elapsed since start of reception.

12. The ultrasound probe of claim 9, wherein the signal output unit includes a wireless communication unit which outputs the signal to an external device through wireless communication.

13. The ultrasound probe of claim 9, further comprising:
a transmission drive unit which outputs pulse signals to the piezoelectric devices to cause the piezoelectric devices to output ultrasound waves of a predetermined wave length; and
a transmission/reception switching drive unit which alternately connects the piezoelectric devices with the transmission drive unit or the phasing adder in response to a control signal.

14. An acoustic sensor, comprising:
the phasing adder of claim 1;
the plurality of piezoelectric devices which receive ultrasound waves, which generate charges in response to sound pressure of the received ultrasound waves, and which send the charges to the phasing adder to be held in the first holding units of the respective corresponding delay charge transfer units;
a signal amplifier which receives the charges which are subjected to phasing addition and output by the phasing adder, and which amplifies the received charges output by the phasing adder as a voltage signal; and
a signal output unit which outputs the amplified voltage signal,
wherein:
in each piezoelectric device:
a first piezoelectric thin film is laminated directly or indirectly on a semiconductor substrate;
conductivity state of a predetermined region in the semiconductor substrate changes on a basis of a charge amount induced in the first piezoelectric thin film in response to sound pressure incident on the first piezoelectric thin film; and
the piezoelectric device is formed as a semiconductor chip which outputs a signal according to the conductive state to the phasing adder.

15. The acoustic sensor of claim 14, wherein:
the predetermined region is a channel region,
an electrode for switching the conductivity of the channel region in the semiconductor substrate is provided in the semiconductor chip, and
when the channel region is conductive, the first piezoelectric thin film is connected to one end of the channel region so that the conductive state of the channel region is changed due to the charge according to the induced charge amount flows through the channel region.

16. The acoustic sensor of claim 14, wherein:
a second piezoelectric thin film is divided in a plurality of blocks to be arranged at least in one direction, the plurality of blocks corresponding respectively to the first piezoelectric thin films included in the respective piezoelectric devices, and
the semiconductor chips of the respective piezoelectric devices output signals individually or in block units.

17. The acoustic sensor of claim 14, wherein the first piezoelectric thin film is formed of a ferroelectric material, and is formed so that a coercive electric voltage which reverses polarization of the first piezoelectric thin film is smaller than a withhold voltage of the semiconductor chip.

18. The acoustic sensor of claim 17, wherein the semiconductor chip is provided with a voltage applying circuit for setting polarization of the first piezoelectric thin film.

19. The acoustic sensor of claim 18, wherein:
a second piezoelectric thin film is divided in a plurality of blocks to be arranged at least in one direction, the plurality of blocks corresponding respectively to the first piezoelectric thin films included in the respective piezoelectric devices, and
the semiconductor chips of the respective piezoelectric devices output signals individually or in block units, and
the voltage applying circuit is provided so that the polarization is set in block units.

20. The acoustic sensor of claim 18, further comprising a controller which determines the polarization of the first piezoelectric thin film and controls operation of the voltage applying circuit according to the determined polarization.

21. The acoustic sensor of claim 20, wherein the controller determines the polarization according to a process relating to a predetermined spatial correlation performed on a received sound wave.

22. An ultrasound diagnosis apparatus, comprising:
an ultrasound probe utilizing the acoustic sensor of claim 18;
a signal processor which analyzes signals relating to ultrasound waves received by the ultrasound probe; and
an output unit which outputs analysis results of the signal processor in a predetermined format; and
a controller which decides polarization of the first piezoelectric thin film and controls operation of the voltage applying circuit according to the decided polarization.

23. An ultrasound probe comprising:
the acoustic sensor of claim 14.

24. An ultrasound diagnosis apparatus, comprising:
the ultrasound probe of claim 23;
a signal processor which analyzes signals relating to ultrasound waves received by the ultrasound probe; and
an output unit which outputs analysis results of the signal processor in a predetermined format.

25. An acoustic sensor comprising:
the phasing adder of claim 1;
the plurality of piezoelectric devices which receive ultrasound waves, which generate charges in response to sound pressure of the received ultrasound waves, and which send the charges to the phasing adder to be held in the first holding units of the respective corresponding delay charge transfer units;
a signal amplifier which receives the charges which are subjected to phasing addition and output by the phasing adder, and which amplifies the received charges output by the phasing adder as a voltage signal; and
a signal output unit which outputs the amplified voltage signal,
wherein:
in each piezoelectric device:
a piezoelectric thin film is laminated directly or indirectly on a semiconductor substrate,
conductivity state of a predetermined region in the semiconductor substrate changes on a basis of a charge amount induced in the piezoelectric thin film in response to sound pressure incident on the piezoelectric thin film,
the piezoelectric device is formed as a semiconductor chip which outputs a signal according to the conductive state to the phasing adder,
the predetermined region is a channel region, and
by changing conductivity level of the channel region in the semiconductor substrate due to an electric field generated by the induced charge amount, the conductivity state of the channel region is changed.

* * * * *